(12) United States Patent
Caldwell et al.

(10) Patent No.: US 8,956,555 B2
(45) Date of Patent: *Feb. 17, 2015

(54) SILYLETHYNYL PENTACENE COMPOUNDS AND COMPOSITIONS AND METHODS OF MAKING AND USING THE SAME

(75) Inventors: Gregg Alexander Caldwell, Cottage Grove, MN (US); Robert Steven Clough, Saint Paul, MN (US); James Craig Novack, Hudson, WI (US); David Howard Redinger, Oakdale, MN (US); Dennis Edward Vogel, Lake Elmo, MN (US); John E. Anthony, Lexington, KY (US); Marcia M. Payne, Lexington, KY (US)

(73) Assignees: 3M Innovative Properties Company, St. Paul, MN (US); Outrider Technologies, Louisville, KY (US)

( * ) Notice: Subject to any disclaimer, the term of this patent is extended or adjusted under 35 U.S.C. 154(b) by 595 days.

This patent is subject to a terminal disclaimer.

(21) Appl. No.: 12/995,145

(22) PCT Filed: May 29, 2009

(86) PCT No.: PCT/US2009/045667
§ 371 (c)(1),
(2), (4) Date: Dec. 6, 2010

(87) PCT Pub. No.: WO2009/155106
PCT Pub. Date: Dec. 23, 2009

(65) Prior Publication Data
US 2011/0073813 A1      Mar. 31, 2011

Related U.S. Application Data

(60) Provisional application No. 61/057,715, filed on May 30, 2008.

(51) Int. Cl.
*H01B 1/00* (2006.01)
*H01L 29/08* (2006.01)
(Continued)

(52) U.S. Cl.
CPC .......... *C07F 7/0818* (2013.01); *H01L 51/0055* (2013.01); *H01L 51/0094* (2013.01); *H01L 51/0545* (2013.01)
USPC .............. 252/500; 257/40; 556/431; 549/456

(58) Field of Classification Search
CPC ........................... C07F 7/0818; H01L 51/0094
USPC ................... 252/500–521.6; 257/40; 556/431
See application file for complete search history.

(56) References Cited

U.S. PATENT DOCUMENTS

| | | | |
|---|---|---|---|
| 6,664,354 | B2 | 12/2003 | Savu |
| 6,690,029 | B1 | 2/2004 | Anthony et al. |

(Continued)

FOREIGN PATENT DOCUMENTS

| | | |
|---|---|---|
| JP | 2007-158062 A | 6/2007 |
| JP | 2007-299852 A | 11/2007 |

(Continued)

OTHER PUBLICATIONS

International Search Report for PCT/US2010/036559.
(Continued)

*Primary Examiner* — Harold Pyon
*Assistant Examiner* — Jaison Thomas
(74) *Attorney, Agent, or Firm* — Withers & Keys, LLC

(57) ABSTRACT

Silylethynyl pentacenes and compositions containing silylethynyl pentacenes are disclosed. Exemplary pentacene compounds have 6,13-silylethynyl substitution with one or more groups (e.g., R, R' and R") covalently bonded to each Si atom of the silylethynyl groups. Methods of making and using silylethynyl pentacenes and compositions containing silylethynyl pentacenes are also disclosed. Substrates and devices comprising the silylethynyl pentacenes and compositions are also disclosed.

20 Claims, 3 Drawing Sheets

(51) Int. Cl.
  *C07F 7/04* (2006.01)
  *C07D 307/77* (2006.01)
  *C07F 7/08* (2006.01)
  *H01L 51/00* (2006.01)
  *H01L 51/05* (2006.01)

(56) References Cited

U.S. PATENT DOCUMENTS

| | | | |
|---|---|---|---|
| 6,864,396 | B2 | 3/2005 | Smith |
| 7,061,010 | B2 | 6/2006 | Minakata |
| 7,385,221 | B1 | 6/2008 | Anthony |
| 7,498,662 | B2 | 3/2009 | Napierala |
| 7,576,208 | B2 * | 8/2009 | Brown et al. ............ 546/49 |
| 7,666,968 | B2 | 2/2010 | Zhu |
| 7,879,688 | B2 | 2/2011 | Novack |
| 8,232,550 | B2 * | 7/2012 | Clough et al. ............ 257/40 |
| 2003/0116755 | A1 | 6/2003 | Takahashi |
| 2004/0222412 | A1 | 11/2004 | Bai |
| 2006/0220007 | A1 | 10/2006 | Bailey |
| 2006/0267004 | A1 | 11/2006 | Fallis et al. |
| 2007/0102696 | A1 | 5/2007 | Brown et al. |
| 2007/0114516 | A1 | 5/2007 | Napierala |
| 2007/0137520 | A1 | 6/2007 | Brown et al. |
| 2007/0146426 | A1 * | 6/2007 | Nelson et al. ............ 347/44 |
| 2007/0249087 | A1 * | 10/2007 | Zhu et al. ............ 438/99 |
| 2009/0001356 | A1 | 1/2009 | Novack |
| 2010/0270542 | A1 | 10/2010 | Zhu |

FOREIGN PATENT DOCUMENTS

| | | |
|---|---|---|
| WO | 2005055248 | 6/2005 |
| WO | 2006/125504 | 11/2006 |
| WO | 2006119853 | 11/2006 |
| WO | 2007078860 | 7/2007 |
| WO | 2007082584 | 7/2007 |
| WO | 2008107089 | 9/2008 |
| WO | 2008128618 | 10/2008 |
| WO | 2009/155106 | 12/2009 |
| WO | 2009/158201 | 12/2009 |
| WO | 2010/138807 | 2/2010 |

OTHER PUBLICATIONS

International Search Report for PCT/US2009/045667, 5 pgs.
Payne, et al., "Funtionalized Higher Acenes: Hexancene and Heptacene", J. Am. Chem. Soc., vol. 127, pp. 8028-8029.
Jiang, et al., "Design, Synthesis, and Properties of New Derivatives of Pentacene", J. Am. Chem. Soc., vol. 71, pp. 2155-2158.
Benard, et al., "Double-Diels-Alder Strategies to Soluble 2,9-and 2,9,6,13-Tetraethynylpentacenes, Photolytic [4+4] Cycloadditions, and Pentacene Crystal Packing", J.Org. Chem. vol. 72, pp. 7229-7236.
Jackson, et al., "High Mobility Solution Processed 6,13-bis(triisopropyl-silylethynyl) Pentacene Organic Thin FilmTransistors", Appl.Phys.Sci., Letters 91, 2007, pp. 063514-1-063514-3.
Kaur, et al. "Exploiting Substituent Effects for the Synthesis of a Photooxidatively Resistant Heptacene Derivative", J. Am. Chem. So. vol. 131, pp. 3424-3425, 2009.
Lim et al., "Control of the Morphology and Structural Development of Solution-Processed Functionalized Acenes of High-Performance Organic Transistor," Adv. Funct. Materials, vol. 19, pp. 1515-1525, 2009.
Qingxin, et al., "Organic Transistors of Small Molecular Weight Materials", Progress in Chemistry, vol. 18, No. 11, pp. 1540-1553, 2006.
International Search Report for PCT/US2010/036559, Jul. 28, 2010.
Gundlach, "Contact-induced Crystallinity for High-performance Soluble Acne-based Transistors and Circuits", Nature Materials, Mar. 2008, vol. 7, No. 3, pp. 216-221.
Payne, "Organic Field-Effect Transistors from Solution-Deposited Functionalized Acenes with Mobilities as High as 1 cm2/V•s", Journal of the American Chemical Society, Apr. 13, 2005, vol. 127, No. 14, pp. 4986-4987.
International Search Report for PCT/US2009/045667, 5 pgs, Nov. 2, 2009.
Kim, et al., "High-Mobility Organic Transistors based on Single Crystalline Microribbons of Triisopropylsilylethynyl Pentacene via Solution-Phase Self Assembly", Adv. Materials, vol. 19, No. 5 2007, pp. 678-682, 680.
Anthony J.E., et al., "A Road Map to Stable, Soluble, Easily Crystallized Pentacene Derivatives", Organic Letters, vol. 4, No. 1, 2002, pp. 15-18.
Payne, et al., "Robust, Soluble Pentacene Ethers", Organic Letters, vol. 6, No. 10, 2004, pp. 1609-1612.
Swartz, et al., "Synthesis and Characterization of Electron-Deficient Pentacenes", Organic Letters, vol. 7, No. 15, 2005, pp. 3163-3166.
Wobkenberg, et al., "Low-Voltage Organic Transistors based on Solution Processed Semiconductors and Self-Assembled Monolayer Gate Dielectrics", Applied Physics Letters, vol. 93, 2008.
Payne, et al., "Funtionalized Higher Acenes: Hexancene and Heptacene", J. Am. Chem. Soc., vol. 127, pp. 8028-8029, 2005.
Jiang, et al., "Design, Synthesis, and Properties of New Derivatives of Pentacene", J. Org. Chem. Soc., vol. 71, pp. 2155-2158, 2006.
Benard, et al., "Double-Diels-Alder Strategies to Soluble 2,9-and 2,9,6,13-Tetraethynylpentacenes, Photolytic [4+4] Cycloadditions, and Pentacene Crystal Packing", J.Org. Chem. vol. 72, pp. 7229-7236, 2007.
Lehnherr et al., "Pentacene Oligomers and Polymers: Functionalization of Pentacene to Afford Mono-, Di-, Tri-, and Polymeric Materials", Organic Letters, vol. 9, No. 22, 2007, pp. 4583-4586.
Okamoto, et al., "Synthesis of Solution-Soluble Pentacene-Containing Conjugated Coploymers", J. Am. Chem. Soc., vol. 129, 2007, pp. 10308-10309.
Jackson, et al., "High Mobility Solution Processed 6,13-bis(triisopropyl-silylethynyl) Pentacene Organic Thin Film Transistors", Appl.Phys.Sci., Letters 91, 2007, pp. 063514-1-063514-3.
Chen, et al., "Morphology and Molecular Orientation of Thin-Film bis(triisopropylsilylethynyl) Pentacene", Materials Rsrch. Soc., vol. 22, No. 6, 2007, pp. 1701-1709.
Palayangoda, et al., "Synthesis of Highly Soluble and Oxidatively Stable Tetraceno[2,3-b]thiopheses and Pentacenes", J. Org. Chem., vol. 72, 2007, pp. 6584-6587.
Anthony, J.E., "Funtionalized Acenes and Heteroacenes for Organic Electronics", Chem. Rev., vol. 106, 2006, pp. 5028-5048.
Payne, et al., "Stable, Crystalline Acenedithiophenes with up to Seven Linearly Fused Rings", Organic Letters, vol. 6, No. 19, 2004, pp. 3325-3328.

* cited by examiner

SILYLETHYNYL PENTACENE COMPOUNDS AND COMPOSITIONS AND METHODS OF MAKING AND USING THE SAME

The present application is a national phase patent application corresponding to international patent application serial no. PCT/US2009/045667 entitled "SILYLETHYNYL PENTACENE COMPOUNDS AND COMPOSITIONS AND METHODS OF MAKING AND USING THE SAME" and filed on May 29, 2009, and claims the benefit of priority to (i) international patent application serial no. PCT/US2009/045667 and (ii) U.S. provisional patent application Ser. No. 61/057,715 entitled "SILYLETHYNYL PENTACENE COMPOUNDS AND COMPOSITIONS AND METHODS OF MAKING AND USING THE SAME" filed on May 30, 2008, the subject matter of both of which is incorporated herein by reference in its entirety.

FIELD OF THE INVENTION

The present invention is related generally to silylethynyl pentacenes and compositions containing silylethynyl pentacenes. The present invention is further related generally to methods of making and using silylethynyl pentacenes, as well as compositions containing silylethynyl pentacenes.

BACKGROUND OF THE INVENTION

Electronic devices composed of organic-based transistors can be manufactured at lower cost and applied to a larger area format than their inorganic counterparts albeit with reduced performance. In general, organic-based transistors utilize either small molecules or polymers as the semiconductor material. Typically, small molecule semiconductor materials have low solubility in organic solvents and thus require a vacuum deposition method to form films. Shadow mask or photolithographic methods are required to pattern multiple layers in order to make useful devices. Vacuum deposition and lithography require processes that cost much more than processes that do not require vacuum deposition and lithography (e.g., solution coating methods).

One cost effective approach of producing inexpensive electronic devices is to apply an organic semiconductor material by any of the following exemplary coating processes: spin coating, knife-coating, roll-to-roll web-coating, and dip coating, as well as printing processes such as ink-jet printing, screen printing, and offset lithography. However, as discussed above, organic semiconductor materials are notoriously insoluble in solvents and those that are soluble are generally unstable in solution. Due to insolubility and instability concerns, the ability to apply organic semiconductor materials using the above-mentioned inexpensive coating steps to form inexpensive electronic devices is limited.

Some organic semiconductors based on pentacene with 6,13-silylethynyl substitution have been shown to (i) be soluble in organic solvents, (ii) be stable in solution, and (iii) provide good performance in organic field effect transistors (OFETs). For example, 6,13-bis[(triisopropylsilyl)ethynyl]pentacene (i.e., also referred to herein as "TIPS-pentacene") has been shown to (i) have a degree of solubility in organic solvents, (ii) have a degree of stability when in solution, and (iii) provide good performance in organic field effect transistors (OFETs). However, even TIPS-pentacene provides limited solubility in some organic solvents, as well as limited performance in electronic devices (e.g., transistors), for example, as measured in terms of charge carrier mobility values.

SUMMARY OF THE INVENTION

There is a need in the art for organic compounds that provide at least one of the following: (i) enhanced solubility in one or more organic solvents, (ii) enhanced stability when incorporated into a given organic solvent, and (iii) enhanced performance when incorporated into an electronic device as a semiconductor layer as measured, for example, by the charge carrier mobility value of the electronic device.

The present invention addresses some of the problems in the art by the discovery of organic compounds, namely, pentacene compounds with 6,13-silylethynyl substitution, having one or more of the following properties: (i) enhanced solubility in one or more organic solvents (e.g., toluene), (ii) enhanced stability when incorporated into a given organic solvent (e.g., toluene), and (iii) enhanced performance when incorporated into an electronic device as a semiconductor layer as measured by the charge carrier mobility value of the electronic device. The pentacene compounds of the present invention may be utilized in coatable compositions in the production of electronic devices. Further, the resulting electronic device may exhibit a charge carrier mobility value of greater than about 2.0 cm$^2$/V-s or higher (e.g., greater than about 2.4 cm$^2$/V-s, greater than about 3.0 cm$^2$/V-s, or higher).

The present invention is directed to pentacene compounds with specific 6,13-silylethynyl substitution. In one exemplary embodiment, the present invention is directed to pentacene compounds having a chemical structure:

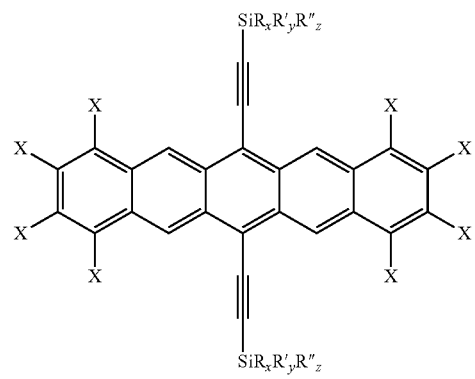

(also referred to hereinafter as "Structure A")

wherein:
each R independently comprises (i) a branched or unbranched, substituted or unsubstituted alkyl group, (ii) a substituted or unsubstituted cycloalkyl group, or (iii) a substituted or unsubstituted cycloalkylalkylene group;
each R' independently comprises (i) a branched or unbranched, substituted or unsubstituted alkenyl group, (ii) a substituted or unsubstituted cycloalkyl group, or (iii) a substituted or unsubstituted cycloalkylalkylene group;
R" comprises (i) hydrogen, (ii) a branched or unbranched, substituted or unsubstituted alkynyl group, (iii) a substituted or unsubstituted cycloalkyl group, (iv) a substituted or unsubstituted cycloalkylalkylene group, (v) a substituted aryl group, (vi) a substituted or unsubstituted arylalkylene group, (vii) an acetyl group, or (viii) a substituted or unsubstituted heterocyclic ring comprising at least one of O, N, S and Se in the ring;
x=1 or 2;
y=1 or 2;
z=0 or 1;
(x+y+z)=3; and each X independently comprises (i) hydrogen, (ii) a halogen, (iii) a branched or unbranched, substituted or unsubstituted alkyl group, (iv) a substituted or unsubstituted aryl group, (v) a branched or unbranched, substituted or unsubstituted alkenyl group, (vi) a branched or unbranched, substituted or unsubstituted alkynyl group, (vii) a substituted or unsubstituted heterocyclic group, (viii) a cyano group, (iv) an ether group, (x) a branched or unbranched, substituted or unsubstituted alkoxy group, (xi) a nitro group, or (xii) any two adjacent X groups form (a) a substituted or unsubstituted carbocyclic ring or (b) a substituted or unsubstituted heterocyclic ring;

wherein when z=0 and R and R' together comprise a combination of (i) branched or unbranched, substituted or unsubstituted alkyl group(s) and (ii) branched or unbranched, substituted or unsubstituted alkenyl group(s), the pentacene compound enables formation of a semiconductor layer having a charge carrier maximum mobility value greater than or equal to 2.0 $cm^2$/V-s as measured by the Transistor Fabrication & Charge Carrier Mobility Value Test Method of the present invention (described below), also referred to herein as the "TF&CCMV Test Method."

In another exemplary embodiment, the present invention is directed to pentacene compounds having Structure A above wherein R, R' and X are as defined above; R" comprises (i) a branched or unbranched, substituted or unsubstituted alkynyl group, (ii) a substituted or unsubstituted cycloalkyl group, (iii) a substituted or unsubstituted cycloalkylalkylene group, (iv) a substituted aryl group, (v) a substituted or unsubstituted arylalkylene group, (vi) an acetyl group, or (vii) a substituted or unsubstituted heterocyclic ring comprising at least one of O, N, S and Se in the ring; and x=y=z=1.

In yet another exemplary embodiment, the present invention is directed to pentacene compounds having Structure A above wherein R, R' and X are as defined above; R" comprises (i) a branched or unbranched, substituted or unsubstituted alkynyl group, (ii) a substituted or unsubstituted cycloalkyl group, (iii) a substituted or unsubstituted cycloalkylalkylene group, (iv) a substituted aryl group, (v) a substituted or unsubstituted arylalkylene group, (vi) an acetyl group, or (vii) a substituted or unsubstituted heterocyclic ring comprising at least one of O, N, S and Se in the ring; (x+y+z)=3; and x or y=2, and z=1.

In yet another exemplary embodiment, the present invention is directed to pentacene compounds having Structure A above wherein R, R', R", x, y, z, and X are as defined above, and at least one of R or R' comprises (i) a substituted or unsubstituted cycloalkyl group or (ii) a substituted or unsubstituted cycloalkylalkylene group. In some embodiment, the pentacene compounds having Structure A above wherein (a) R, R', R", x, y, z, and X are as defined above, (b) at least one of R or R' comprises (i) a substituted or unsubstituted cycloalkyl group or (ii) a substituted or unsubstituted cycloalkylalkylene group, and (c) the remaining groups (i.e., R, R', R") comprise either (i) branched or unbranched, substituted or unsubstituted alkyl group(s) and (ii) branched or unbranched, substituted or unsubstituted alkenyl group(s).

The present invention is further directed to compositions comprising (I) at least one pentacene compound having Structure A, wherein R, R', R", x, y, z and X are as described above; and (II) a solvent. The compositions of the present invention may comprise the at least one pentacene compound and solvent alone or in combination with one or more additional composition components, such as a polymer additive.

The present invention is even further directed to a substrate having at least one coatable surface and a coated layer on the at least one coatable surface, wherein the coated layer comprises a pentacene compound having Structure A, wherein R, R', R", x, y, z and X are as described above. In one exemplary embodiment, the substrate comprises an electronic device or an electronic device component.

The present invention is also directed to electronic devices comprising a coated layer, wherein the coated layer comprises a pentacene compound having Structure A, wherein R, R', R", x, y, z and X are as described above; wherein the electronic device has a charge carrier mobility value greater than or equal to 2.0 $cm^2$/V-s.

The present invention is also directed to methods of making pentacene compounds having Structure A, wherein R, R', R", x, y, z and X are as described above.

The present invention is further directed to methods of using one or more pentacene compounds to form compositions (e.g., ink jet printable compositions), coatings, substrates having a coated layer thereon, electronic device components, and electronic devices, wherein at least one pentacene compound has Structure A, wherein R, R', R", x, y, z and X are as described above.

These and other features and advantages of the present invention will become apparent after a review of the following detailed description of the disclosed embodiments and the appended claims.

BRIEF DESCRIPTION OF THE DRAWINGS

The present invention is further described with reference to the appended figures, wherein.

DETAILED DESCRIPTION OF THE INVENTION

Figure 1:
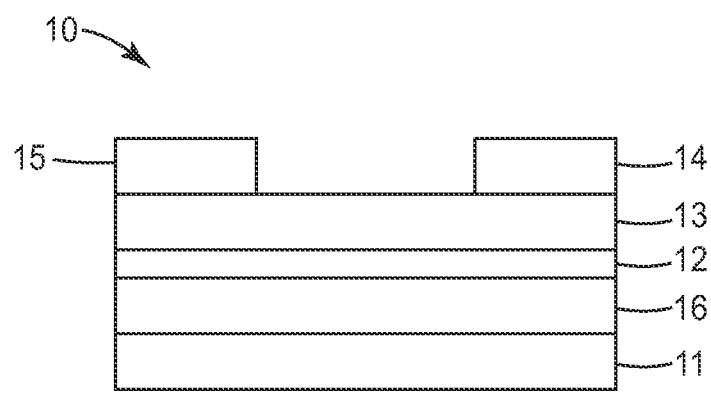
FIG. 1 is a cross-sectional view of an exemplary thin film transistor comprising a semiconductor layer formed via solution deposition of a composition containing at least one pentacene compound of the present invention.

The present invention is directed to pentacene compounds having a chemical structure (also referred to herein as "Structure A"):

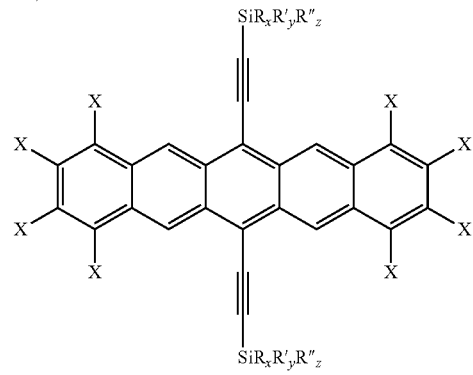

wherein:

each R independently comprises (i) a branched or unbranched, substituted or unsubstituted alkyl group, (ii) a substituted or unsubstituted cycloalkyl group, or (iii) a substituted or unsubstituted cycloalkylalkylene group;

each R' independently comprises (i) a branched or unbranched, substituted or unsubstituted alkenyl group, (ii) a substituted or unsubstituted cycloalkyl group, or (iii) a substituted or unsubstituted cycloalkylalkylene group;

R" comprises (i) hydrogen, (ii) a branched or unbranched, substituted or unsubstituted alkynyl group, (iii) a substituted or unsubstituted cycloalkyl group, (iv) a substituted or unsubstituted cycloalkylalkylene group, (v) a substituted aryl group, (vi) a substituted or unsubstituted arylalkylene group, (vii) an acetyl group, or (viii) a substituted or unsubstituted heterocyclic ring comprising at least one of O, N, S and Se in the ring;

x=1 or 2;

y=1 or 2;

z=0 or 1;

(x+y+z)=3; and each X independently comprises (i) hydrogen, (ii) a halogen, (iii) a branched or unbranched, substituted or unsubstituted alkyl group, (iv) a substituted or unsubstituted aryl group, (v) a branched or unbranched, substituted or unsubstituted alkenyl group, (vi) a branched or unbranched, substituted or unsubstituted alkynyl group, (vii) a substituted or unsubstituted heterocyclic group, (viii) a cyano group, (iv) an ether group, (x) a branched or unbranched, substituted or unsubstituted alkoxy group, (xi) a nitro group, or (xii) any two adjacent X groups form (a) a substituted or unsubstituted carbocyclic ring or (b) a substituted or unsubstituted heterocyclic ring;

wherein when z=0 and R and R' together comprise a combination of (i) branched or unbranched, substituted or unsubstituted C1-C8 alkyl group(s) and (ii) branched or unbranched, substituted or unsubstituted C2-C8 alkenyl group(s), the pentacene compound enables formation of a semiconductor layer having a maximum charge carrier mobility value greater than or equal to 2.0 $cm^2/V$-s as measured by the Transistor Fabrication & Charge Carrier Mobility Value Test Method of the present invention (described below).

A number of terms are used to describe the pentacene compounds of the present invention. As used herein, the various terms are defined as follows:

"a substituted alkyl group" refers to an alkyl group having one or more substituents thereon, wherein each of the one or more substituents comprises a monovalent moiety containing one or more atoms other than carbon and hydrogen either alone (e.g., a halogen such as F) or in combination with carbon (e.g., a cyano group) and/or hydrogen atoms (e.g., a hydroxyl group or a carboxylic acid group);

"a substituted alkenyl group" refers to an alkenyl group having (i) one or more C=C double bonds, and (ii) one or more substituents thereon, wherein each of the one or more substituents comprises a monovalent moiety containing one or more atoms other than carbon and hydrogen either alone or in combination with carbon and/or hydrogen atoms;

"a substituted alkynyl group" refers to an alkynyl group having (i) one or more C—C triple bonds, and (ii) one or more substituents thereon, wherein each of the one or more substituents comprises a monovalent moiety containing one or more atoms other than carbon and hydrogen (e.g., Si) either alone or in combination with carbon and/or hydrogen atoms;

"a cycloalkyl group" refers to a ring structure consisting of 3 or more carbon atoms in the ring structure (i.e., only carbon atoms in the ring structure) wherein a carbon atom of the ring structure is bonded directly to the silicon atom of the silyl group;

"a substituted cycloalkyl group" refers to a cycloalkyl group having one or more substituents thereon, wherein each of the one or more substituents comprises a monovalent moiety containing one or more atoms (e.g., a halogen such as F, an alkyl group, a cyano group, a hydroxyl group, or a carboxylic acid group);

"a cycloalkylalkylene group" refers to a ring structure consisting of 3 or more carbon atoms in the ring structure (i.e., only carbon atoms in the ring structure) wherein the ring structure is separated from the silicon atom of the silyl group by a divalent alkyl spacer group having one or more carbon atoms (typically, from 1 to 3 carbon atoms, more typically, 1 carbon atom);

"a substituted cycloalkylalkylene group" refers to a cycloalkylalkylene group having one or more substituents thereon, wherein each of the one or more substituents comprises a monovalent moiety containing one or more atoms (e.g., a halogen such as F, an alkyl group, a cyano group, a hydroxyl group, or a carboxylic acid group);

"a substituted aryl group" refers to an aromatic ring structure consisting of 5 to 10 carbon atoms in the ring structure (i.e., only carbon atoms in the ring structure), wherein a carbon atom of the ring structure is bonded directly to the silicon atom of the silyl group, and the ring structure has one or more substituents thereon, wherein each of the one or more substituents comprises a monovalent moiety containing one or more atoms (e.g., a halogen such as F, an alkyl group, a cyano group, a hydroxyl group, or a carboxylic acid group);

"an arylalkylene group" refers to an aromatic ring structure consisting of 5 to 10 carbon atoms in the ring structure (i.e., only carbon atoms in the ring structure), wherein the aromatic ring structure is separated from the silicon atom of the silyl group by a divalent alkylene spacer group having one or more carbon atoms (typically, from 1 to 3 carbon atoms, more typically, 1 carbon atom);

"a substituted arylalkylene group" refers to an arylalkylene group having one or more substituents thereon, wherein each of the one or more substituents comprises a monovalent moiety containing one or more atoms (e.g., a halogen such as F, an alkyl group, a cyano group, a hydroxyl group, or a carboxylic acid group);

"a substituted heterocyclic ring" or "a substituted heterocyclic group" refers to a heterocyclic ring (i.e., a saturated, partially saturated, or unsaturated heterocyclic ring) comprising at least one of O, N, S and Se in the ring structure, and having one or more substituents bonded to one or more members of the ring structure, wherein the heterocyclic ring can be aromatic or non-aromatic and wherein each of the one or more substituents comprises a monovalent moiety containing one or more atoms (e.g., a halogen such as F, an alkyl group, a cyano group, a hydroxyl group, or a carboxylic acid group);

"a substituted carbocyclic ring" refers to a ring (i.e., a saturated, partially saturated, or unsaturated carbocyclic ring) comprising C in the ring structure, and having one or more substituents bonded to one or more members of the ring structure, wherein each of the one or more substituents comprises a monovalent moiety containing one or more atoms (e.g., a halogen such as F, an alkyl group, a cyano group, a hydroxyl group, or a carboxylic acid group);

"a substituted alkoxy group" refers to an alkoxy group having one or more substituents thereon, wherein each of the one or more substituents comprises a monovalent moiety containing one or more atoms other than carbon and hydrogen either alone (e.g., a halogen such as F) or in combination with carbon (e.g., a cyano group) and/or hydrogen atoms (e.g., a hydroxyl group or a carboxylic acid group);

"an ether group" refers to a —$R_a$—O—$R_b$ radical wherein $R_a$ a branched or unbranched alkylene, arylene, alkylarylene or arylalkylene hydrocarbon and $R_b$ is a branched or unbranched alkyl, aryl, alkylaryl or arylalkyl hydrocarbon;

"charge carrier mobility value" refers to the drift velocity of a charge carrier (cm/s) per unit applied field (V/cm) with resulting measurement units of "$cm^2/V\text{-}s$" as measured using any test method for measuring the drift velocity of a charge carrier;

"charge carrier mobility value as measured by Mobility Value Test Method I" or "charge carrier mobility value as measured by Mobility Value Test Method II" refers to the charge carrier mobility value of an electronic device measured using the specific Mobility Value Test Method I or Mobility Value Test Method II as described in the Test Method section of the examples below; and "charge carrier mobility value as measured by the Transistor Fabrication & Charge Carrier Mobility Value Test Method" or "charge carrier mobility value as measured by the TF&CCMV Test Method" refers to the charge carrier mobility value of an electronic device that is fabricated using a specific device construction, specific device materials, and a specific device fabrication method, and is measured using a specific mobility value test method as described in the Test Method section of the examples below.

Pentacene compounds having the above chemical structure have been found to possess at least one of the following properties: (i) increased solubility in various organic solvents, (ii) increased stability in various organic solvents, and (iii) increased charge carrier mobility values when used as a semiconductor layer in electronic devices. By varying the R groups (i.e., R, R' and R") and X groups in the above chemical structure, one can tailor a resulting pentacene compound for a given application (e.g., as a semiconductor layer in an electronic device).

For example, when a given pentacene compound of the present invention is to be used to form a semiconductor layer in an electronic device (e.g., a transistor), the ability of the pentacene compound to exhibit two-dimensional stacking (i.e., 2-D stacking of individual molecules) is an important consideration, which significantly impacts the charge carrier mobility value of the resulting semiconductor layer. The dimensionality of a given stacking configuration may be easily measured by examination of the single-crystal X-ray structure of a given material. A given material exhibiting two-dimensional, or "brickwork" stacking is characterized by having four nearest neighbors with contacts between aromatic carbon atoms lying roughly within the van der Waals radius of carbon (ideally, 3.3-3.6 Å). Considering a simple pentacene unit, any material that has two aromatic close-contact neighbors above the plane of the pentacene ring, and two aromatic close-contact neighbors below the plane of the pentacene ring is typically classified as having two-dimensional interactions or 2-D stacking. It is generally the case that molecules with two-dimensional pi-stacking yield superior thin-film morphologies for field-effect transistor applications, along with improved charge transport in the solid state.

A common alternative case is one-dimensional stacking, where each molecule possesses one stacking neighbor above the plane of the aromatic ring, and one stacking neighbor below the plane of the aromatic ring. The separation between the aromatic faces is preferably within the van der Waals radius of carbon (ideally, 3.3-3.6 Å). In general, materials that exhibit 1-D stacking do not yield high-performance transistors when cast from solution, but these materials do exhibit enhanced performance in photovoltaic devices. Such 1-D stacked materials are suitable for use, for example, as the donor component of a photovoltaic device, or when substituents X are electron-withdrawing groups (e.g., fluoro, fluoroalkyl, cyano or nitro groups), the materials are potentially suitable for use as an acceptor in a photovoltaic device.

Many of the pentacene compounds of the present invention exhibit 2-D or 1-D stacking. It has been discovered that pentacene compounds having the above chemical structure (i.e., Structure A), wherein R, R' and R" together comprise two sterically similar groups and one sterically dissimilar group exhibit 2-D stacking in the crystalline, solid state as shown, for example, by single crystal x-ray analysis. In these compounds, it is believed that the two sterically similar groups are spatially oriented on opposite sides of a plane extending though the five ring structure of the pentacene compound, while the sterically dissimilar group is spatially oriented substantially within or along (i.e., substantially parallel with) the plane containing the five ring structure of the pentacene compound in the crystalline, solid state.

Consequently, in one desired embodiment, the pentacene compounds of the present invention have Structure A, wherein R, R' and R" together comprise two sterically similar groups and one sterically dissimilar group, the two sterically similar groups being oriented on opposite sides of a plane extending though the five ring structure of the pentacene compound, and the sterically dissimilar group being substantially within the plane (i.e., the plane containing the five ring structure of the pentacene compound). In a further desired embodiment, the pentacene compounds of the present invention have Structure A, wherein R, R' and R" together comprise two identical groups and one dissimilar group, the two identical groups being oriented on opposite sides of a plane extending though the five ring structure of the pentacene compound, and the dissimilar group being substantially within the plane (i.e., the plane containing the five ring structure of the pentacene compound).

For example, the pentacene compounds may have two identical groups covalently bonded to the Si atom such as when (a)(i) two R groups independently comprise a branched or unbranched, substituted or unsubstituted alkyl group, or (a)(ii) two R' groups independently comprise a branched or unbranched, substituted or unsubstituted alkenyl group, and (b) the remaining group bonded to the Si atom comprises a substituent other than (i) a branched or unbranched, substituted or unsubstituted alkyl group, and (ii) a branched or unbranched, substituted or unsubstituted alkenyl group. In other embodiments, the pentacene compounds may have two identical groups covalently bonded to the Si atom wherein the identical groups comprise (i) a substituted or unsubstituted cycloalkyl group or (ii) a substituted or unsubstituted cycloalkylalkylene group, and the dissimilar group comprise a substituent other than (i) a substituted or unsubstituted cycloalkyl group and (ii) a substituted or unsubstituted cycloalkylalkylene group (e.g., an allyl group or an isopropyl group).

In some exemplary embodiments, the pentacene compounds have Structure A wherein (a) z=0, (b) each R independently comprises (i) a branched or unbranched, substituted or unsubstituted C1-C8 alkyl group, (ii) a substituted or unsubstituted cycloalkyl group, or (iii) a substituted or unsubstituted cycloalkylalkylene group, and (c) each R' independently comprises a branched or unbranched, substituted or unsubstituted C2-C8 alkenyl group. In these exemplary embodiments, the pentacene compounds may have Structure A wherein (a) z=0, (b) each R independently comprises a branched, unsubstituted alkyl group having n carbon atoms, (c) each R' independently comprises a branched, unsubstituted alkenyl group having n carbon atoms, and (d) 3≤n≤8, more desirably, n=3 or 4.

In some exemplary embodiments, the pentacene compounds have Structure A wherein (i) z=0, (ii) each R independently comprises a branched alkane substituent having n carbon atoms, (iii) each R' independently comprises a branched alkene substituent having n carbon atoms, and (iv) 3≤n≤8. For example, in some embodiments, the pentacene compounds have Structure A wherein R comprises isopropyl, and R' comprises isopropenyl. In some exemplary embodiments, the pentacene compounds of the present invention have one of the following chemical structures:

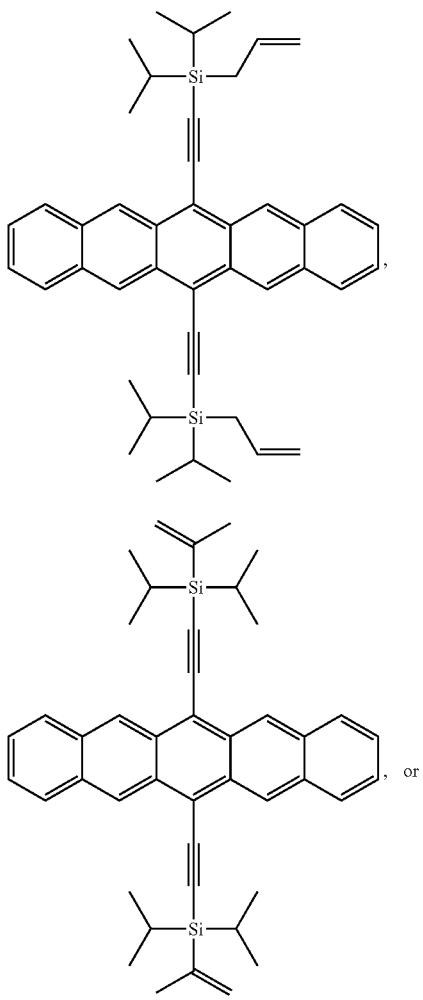

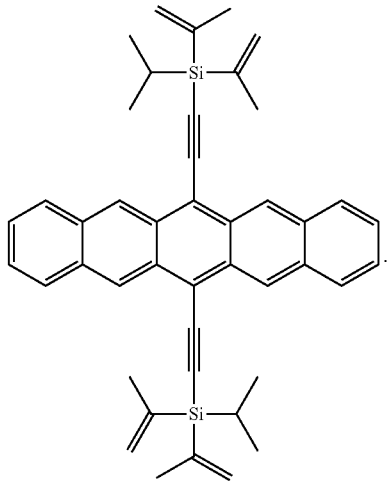

It has been discovered that compounds I and II provide (i) exceptional solubility and stability in a variety or organic solvents, and/or (ii) exceptional mobility values when incorporated into a given electronic device (e.g., a TFT). Compound I, namely, 6,13-bis(allyldiisopropylsilylethynyl)pentacene (also referred to herein as "allyl DIPS"), has been found to exhibit increased solubility in certain organic solvents, such as toluene, compared to known pentacene compounds such as TIPS-pentacene. For example, compound I has a solubility in toluene of up to and greater than about 21 wt %. When used in a semiconductor layer of an electronic device, compound I can provide the semiconductor layer with a maximum charge carrier mobility value of greater than 2.0 $cm^2/V$-s (or greater than about 2.1 $cm^2/V$-s, or greater than about 2.2 $cm^2/V$-s, or greater than about 2.3 $cm^2/V$-s, or greater than about 2.4 $cm^2/V$-s) as measured using the TF&CCMV Test Method (described below).

Compound II, namely, 6,13-bis(isopropenyldiisopropylsilylethynyl)pentacene (also referred to herein as "IP-DIPS"), provides similar advantages over known pentacene compounds such as TIPS-pentacene. When used in a semiconductor layer of an electronic device, compound II can provide the semiconductor layer with a maximum charge carrier mobility value of greater than 3.0 $cm^2/V$-s (or greater than about 3.1 $cm^2/V$-s, or greater than about 3.2 $cm^2/V$-s, or greater than about 3.3 $cm^2/V$-s, or greater than about 3.4 $cm^2/V$-s) as measured using the TF&CCMV Test Method.

In addition to Compounds I, II and III, Table 1 below provides a number of exemplary pentacene compounds of the present invention having the above chemical structure, wherein (i) z=0, and (ii)(a) at least one R group comprises a branched or unbranched, substituted or unsubstituted C1-C8 alkyl group or (ii)(b) at least one R' group comprises a branched or unbranched, substituted or unsubstituted C2-C8 alkenyl group.

As shown in Table 1 below, other exemplary pentacene compounds of the present invention include pentacene compounds having Structure A, wherein (a) z=0, (b) each R independently comprises a branched or unbranched, substituted or unsubstituted alkyl group (for example, a C1-C8 alkyl group), and (c) each R' independently comprises a substituted or unsubstituted cycloalkyl group. For example, desired pentacene compounds have Structure A, wherein (1) two R groups independently comprise isopropyl groups, and R' comprises a substituted or unsubstituted cyclopropyl group or cyclobutyl group, more desirably, a cyclopropyl group, such as Compound IV shown below, or (2) one R group comprises an isopropyl group, and each R' group independently comprises a substituted or unsubstituted cyclopropyl group or cyclobutyl group, more desirably, a cyclopropyl group, such as Compound XIII shown below:

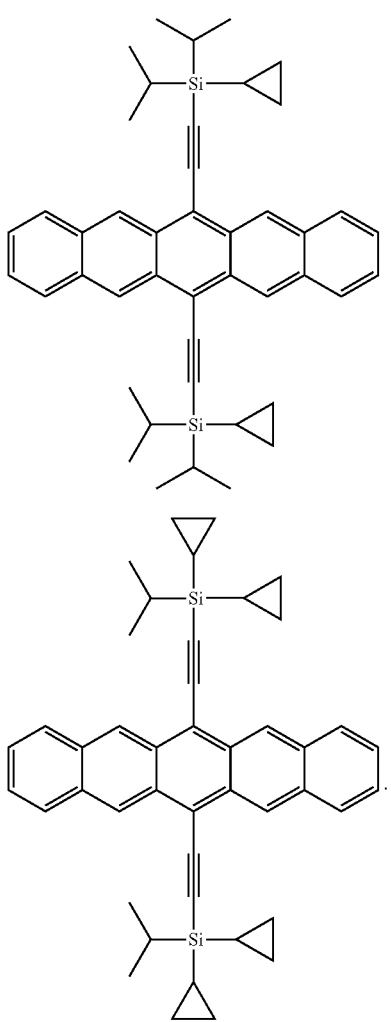

IV

XIII

As shown in Table 1 below, other exemplary pentacene compounds of the present invention include pentacene compounds having Structure A, wherein (a) z=0, (b) each R independently comprises a substituted or unsubstituted cycloalkyl group, and (c) each R' independently comprises a branched or unbranched, substituted or unsubstituted alkenyl group (e.g., a C2-C8 alkenyl group). For example, a given pentacene compound may have Structure A, wherein two R groups independently comprise a substituted or unsubstituted cyclopropyl group or cyclobutyl group, desirably, a cyclopropyl group, and R' comprises a branched or unbranched, substituted or unsubstituted C2-C8 alkenyl group such as, an isopropenyl group or an isopropenyl group having one or more substituents thereon (e.g., one or more F atoms). Another pentacene compound may have Structure A, wherein one R group comprises a substituted or unsubstituted cyclopropyl group or cyclobutyl group, desirably, a cyclopropyl group, and two R' groups comprise branched or unbranched, substituted or unsubstituted C2-C8 alkenyl groups such as, isopropenyl groups or isopropenyl groups having one or more substituents thereon (e.g., one or more F atoms).

Other exemplary pentacene compounds of the present invention include pentacene compounds having Structure A, wherein (a) z=0, (b) each R independently comprises a substituted or unsubstituted cycloalkylalkylene group (e.g., a cyclopropylmethylene group) having a divalent alkylene spacer with from 1 to 3 carbon atoms, typically, 1 carbon atom (e.g., methylene), between each cycloalkane moiety (e.g., cyclopropane) and each silicon atom, and (c) each R' independently comprises a branched or unbranched, substituted or unsubstituted C2-C8 alkenyl group (e.g., an isopropenyl group). Exemplary pentacene compounds may have the above chemical structure, wherein two R groups independently comprise a substituted or unsubstituted cyclopropylmethylene group or cyclobutylmethylene group, desirably, a cyclopropylmethylene group, and R' comprises a branched or unbranched, substituted or unsubstituted C2-C8 alkenyl group such as, an isopropenyl group or an isopropenyl group having one or more substituents thereon (e.g., one or more F atoms). Another pentacene compound may have the above chemical structure, wherein one R group comprises a substituted or unsubstituted cyclopropylmethylene group or cyclobutylmethylene group, desirably, a cyclopropylmethylene group, and two R' groups comprise branched or unbranched, substituted or unsubstituted C2-C8 alkenyl groups such as, isopropenyl groups or isopropenyl groups having one or more substituents thereon (e.g., one or more F atoms). See, exemplary compounds in Table 1 below.

TABLE 1

Exemplary Pentacene Compounds Where z = 0

| Compound | x equals: | y equals: | R is: | R' is: |
|---|---|---|---|---|
| I | 2 | 1 | isopropyl/isopropyl | allyl |
| II | 2 | 1 | isopropyl/isopropyl | isopropenyl |
| III | 1 | 2 | isopropyl | isopropenyl/isopropenyl |
| IV | 2 | 1 | isopropyl/isopropyl | cyclopropyl |
| VI | 2 | 1 | isopropyl/isopropyl | 2,3-dimethylcyclopropyl |
| VII | 2 | 1 | isopropyl/isopropyl | 2,2,3,3-tetramethylcyclopropyl |
| VIII | 2 | 1 | isopropyl/isopropyl | cyclobutyl |
| IX | 2 | 1 | isopropyl/isopropyl | cyclopentyl |
| X | 2 | 1 | isopropyl/isopropyl | 2-but-1-enyl |
| XI | 2 | 1 | isopropyl/isopropyl | cis-2-but-2-enyl |
| XII | 2 | 1 | isopropyl/isopropyl | 3-but-1-enyl |
| XIII | 1 | 2 | isopropyl | cyclopropyl/cyclopropyl |
| XV | 1 | 2 | isopropyl | allyl/allyl |
| XVI | 1 | 2 | cyclopropyl | isopropenyl/isopropenyl |
| XVIII | 1 | 2 | 2,3-dimethylcyclopropyl | isopropenyl/isopropenyl |
| XIX | 1 | 2 | 2,2,3,3-tetramethylcyclopropyl | isopropenyl/isopropenyl |
| XX | 1 | 2 | cyclobutyl | isopropenyl/isopropenyl |
| XXI | 1 | 2 | cyclopentyl | isopropenyl/isopropenyl |
| XXII | 1 | 2 | 2-but-1-enyl | isopropenyl/isopropenyl |

Other exemplary pentacene compounds of the present invention include pentacene compounds having Structure A, wherein (a) x or y=2, and (b) z=1. A number of exemplary pentacene compounds of the present invention having this type of silyl substitution are shown in Table 2 below.

As shown in Table 2, exemplary pentacene compound of the present invention include pentacene compounds having Structure A, wherein (a) each R independently comprises a branched or unbranched, substituted or unsubstituted C1-C8 alkyl group; (b) each R' independently comprises a branched or unbranched, substituted or unsubstituted C2-C8 alkenyl group; and (c) R" comprises (i) a branched or unbranched, substituted or unsubstituted C2-C8 alkynyl group, (ii) a substituted aryl group, (iii) a substituted or unsubstituted arylalkylene group, (iv) an acetyl group, or (v) a substituted or unsubstituted heterocyclic ring comprising at least one of O, N, S and Se in the ring. Desirably, the pentacene compounds have Structure A, wherein (a) each R independently comprises a branched or unbranched, substituted or unsubstituted C1-C8 alkyl group (or C1-C4 alkyl group); (b) each R' independently comprises a branched or unbranched, substituted or unsubstituted C2-C8 alkenyl group (or C2-C4 alkenyl group); and (c) R" comprises (i) a branched or unbranched, substituted or unsubstituted C2-C8 alkynyl group, (ii) a substituted aryl group, (iii) a substituted or unsubstituted arylalkylene group, (iv) an acetyl group, or (v) a substituted or unsubstituted heterocyclic ring comprising at least one of O, N, S and Se in the ring.

In one exemplary embodiment, pentacene compounds of the present invention include pentacene compounds having Structure A, wherein (a) each R independently comprises a branched or unbranched, substituted or unsubstituted C1-C8 alkyl group (or C1-C4 alkyl group such as an isopropyl group); (b) each R' independently comprises a branched or unbranched, substituted or unsubstituted C2-C8 alkenyl group (or C2-C4 alkenyl group such as an allyl group); and (c) R" comprises a substituted or unsubstituted aryl group (e.g., a p-tolyl group or p-methoxyphenyl). See, for example, exemplary compounds XXIV and XXXII in Table 2.

In another exemplary embodiment, pentacene compounds of the present invention include pentacene compounds having Structure A, wherein (a) each R independently comprises a branched or unbranched, substituted or unsubstituted C1-C8 alkyl group (or C1-C4 alkyl group such as an isopropyl group); (b) each R' independently comprises a branched or unbranched, substituted or unsubstituted C2-C8 alkenyl group (or C2-C4 alkenyl group such as an allyl group); and (c) R" comprises a substituted or unsubstituted arylalkylene group having a divalent alkylene spacer with from 1 to 3 carbon atoms between each aryl moiety and each silicon atom (e.g., a benzyl group). See, for example, exemplary compounds XXV and XXXIII in Table 2.

Other exemplary pentacene compounds of the present invention include pentacene compounds having Structure A, wherein (a) each R independently comprises a branched or unbranched, substituted or unsubstituted C1-C8 alkyl group (or C1-C4 alkyl group such as an isopropyl group); (b) each R' independently comprises a branched or unbranched, substituted or unsubstituted C2-C8 alkenyl group (or C2-C4 alkenyl group such as an allyl group); and (c) R" comprises an acetyl group. See, for example, exemplary compounds XXVI and XXXIV in Table 2.

Other exemplary pentacene compounds of the present invention include pentacene compounds having Structure A, wherein (a) each R independently comprises a branched or unbranched, substituted or unsubstituted C1-C8 alkyl group (or C1-C4 alkyl group such as an isopropyl group); (b) each R' independently comprises a branched or unbranched, substituted or unsubstituted C2-C8 alkenyl group (or C2-C4 alkenyl group such as an ally group); and (c) R" comprises a substituted or unsubstituted heterocyclic ring comprising at least one of O, N, S and Se in the ring. See, for example, exemplary compounds XXVII to XXX and XXXV to XXXVIII in Table 2.

TABLE 2

Exemplary Pentacene Compounds Where x or y = 2 and z = 1

| Compound | x equals: | y equals: | R or R' is: | R" is: |
|---|---|---|---|---|
| XXIII | 2 | 0 | isopropyl/isopropyl | propynyl |
| XXIV | 2 | 0 | isopropyl/isopropyl | p-tolyl |
| XXV | 2 | 0 | isopropyl/isopropyl | benzyl |
| XXVI | 2 | 0 | isopropyl/isopropyl | acetyl |
| XXVII | 2 | 0 | isopropyl/isopropyl | 2-furanyl |
| XXVIII | 2 | 0 | isopropyl/isopropyl | N-methylpyrrol-2-yl |
| XXIX | 2 | 0 | isopropyl/isopropyl | 2-thienyl |
| XXX | 2 | 0 | isopropyl/isopropyl | 2-selenophenyl |
| XXXI | 0 | 2 | allyl/allyl | propynyl |
| XXXII | 0 | 2 | allyl/allyl | p-tolyl |
| XXXIII | 0 | 2 | allyl/allyl | benzyl |
| XXXIV | 0 | 2 | allyl/allyl | acetyl |
| XXXV | 0 | 2 | allyl/allyl | 2-furanyl |
| XXXVI | 0 | 2 | allyl/allyl | N-methylpyrrol-2-yl |
| XXXVII | 0 | 2 | allyl/allyl | 2-thienyl |
| XXXVIII | 0 | 2 | allyl/allyl | 2-selenophenyl |

Although not shown in Table 2, it should be noted that other pentacene compounds of the present invention may have Structure A, wherein the substituted or unsubstituted heterocyclic ring comprising at least one of O, N, S and Se in the ring comprises a substituted or unsubstituted furanyl group, a substituted or unsubstituted pyrrolyl group, a substituted or unsubstituted thienyl group, or a substituted or unsubstituted selenophenyl group.

Other exemplary pentacene compounds of the present invention include pentacene compounds having Structure A, wherein (a) x=1, (b) y=1, and (c) z=1. A number of exemplary pentacene compounds of the present invention having this type of silyl substitution are shown in Table 3 below.

As shown in Table 3, exemplary pentacene compounds of the present invention include pentacene compounds having three different R groups (e.g., R, R' and R") bonded to the silicon atom of a given silyl group. Such pentacene compounds may be tailored to provide a combination of features based on the various R groups. For example, an allyl group may be used to increase solubility of the resulting pentacene compound in a given solvent (e.g., toluene), while a cyclopropyl group may be used in to increase a mobility value. In other embodiments, three similar R groups may be utilized (e.g., three cyclopropyl groups).

TABLE 3

Exemplary Pentacene Compounds Where x, y and z = 1

| Compound | R is: | R' is: | R" is: |
|---|---|---|---|
| XXXIX | isopropyl | allyl | propynyl |
| XL | isopropyl | allyl | p-tolyl |
| XLI | isopropyl | allyl | benzyl |
| XLII | isopropyl | allyl | acetyl |
| XLIII | isopropyl | allyl | 2-furanyl |
| XLIV | isopropyl | allyl | N-methylpyrrol-2-yl |
| XLV | isopropyl | allyl | 2-thienyl |
| XLVI | isopropyl | allyl | 2-selenophenyl |
| XLVII | isopropyl | allyl | cyclopropyl |
| XLIX | isopropyl | allyl | 2,3-dimethylcyclopropyl |
| L | isopropyl | allyl | 2,2,3,3-tetramethylcyclopropyl |
| LI | isopropyl | allyl | cyclobutyl |
| LII | cyclopropyl | cyclopropyl | cyclopropyl |
| LIII | p-tolyl | p-tolyl | p-tolyl |
| LIV | benzyl | benzyl | benzyl |

A few exemplary structures of compounds of the present invention are provided below:

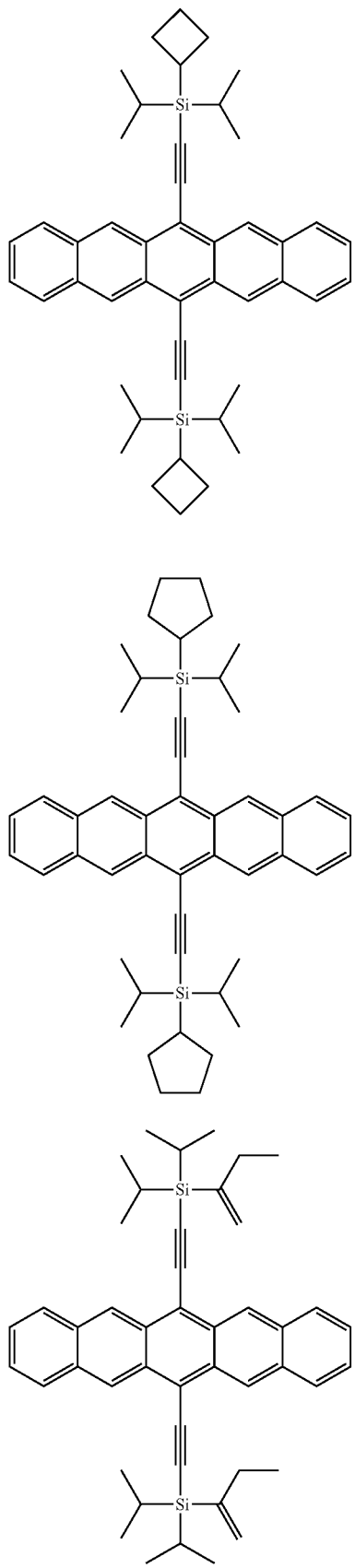
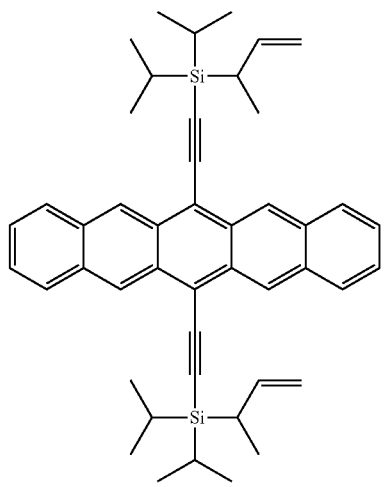
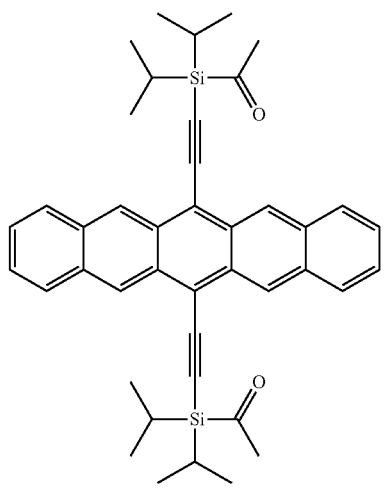
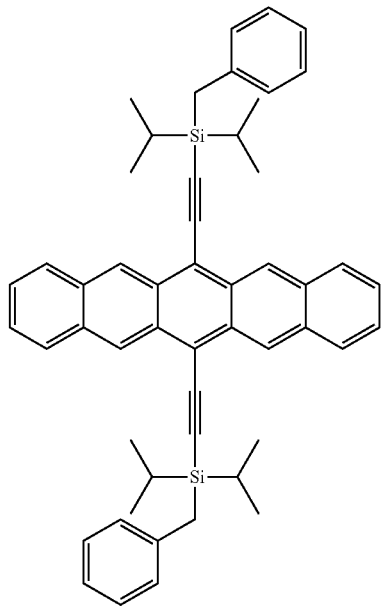

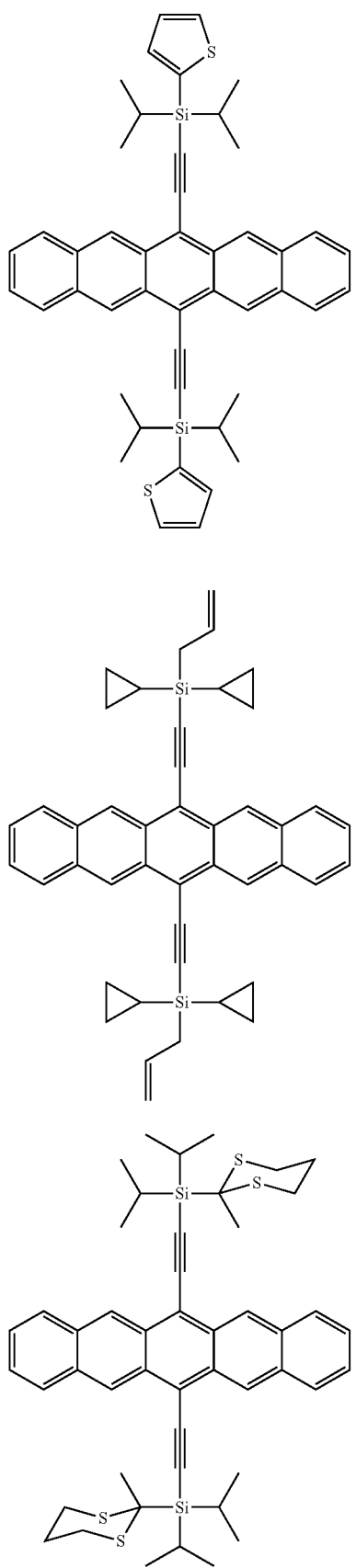
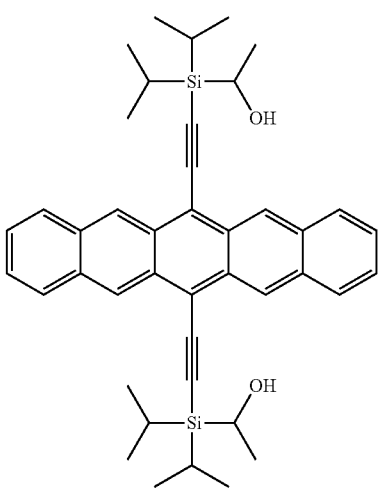
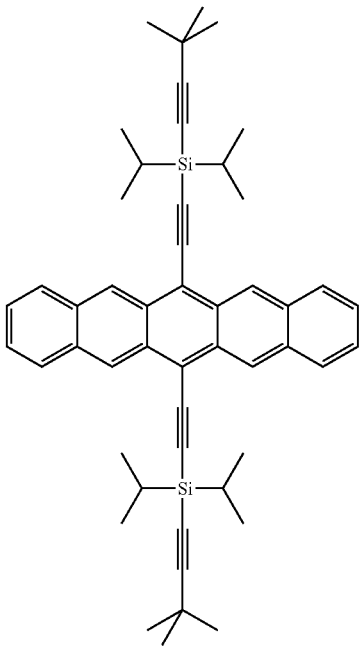

-continued

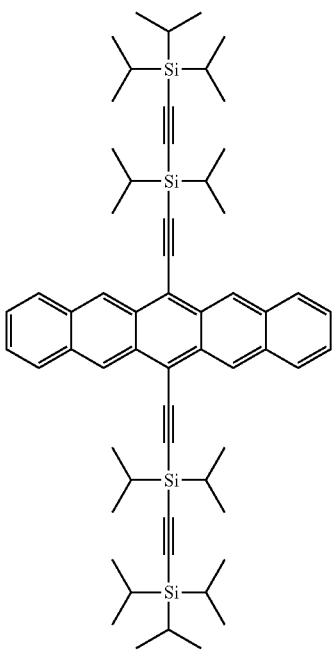

LIX wherein:
VIII=6,13-Bis[(cyclobutyl diisopropylsilyl)ethynyl]pentacene;
IX=6,13-Bis[(cyclopentyl diisopropylsilyl)ethynyl]pentacene;
X=6,13-Bis[(2-but-1-enyl diisopropylsilyl)ethynyl]pentacene;
XI=6,13-Bis[(3-but-1-enyl diisopropylsilyl)ethynyl]pentacene;
XXVI=6,13-Bis[(acetyl diisopropylsilyl)ethynyl]pentacene;
XXV=6,13-Bis[(benzyl diisopropylsilyl)ethynyl]pentacene;
XXIX=6,13-Bis[(2-thienyl diisopropylsilyl)ethynyl]pentacene;
LV=6,13-Bis[(allyl dicyclopropylsilyl)ethynyl]pentacene;
LVI=6,13-Bis[((2-(1,3-dithianyl)ethyl, diisopropylsilyl)ethynyl]pentacene;
LVII=6,13-Bis[(1-hydroxyethyl diisopropylsilyl)ethynyl]pentacene;
LVIII=6,13-Bis[(3,3-dimethylbut-1-ynyl diisopropylsilyl)ethynyl]pentacene; and
LIX=6,13-Bis[(triisopropylsilylethynyl diisopropylsilyl)ethynyl]pentacene.

As discussed above, the present invention is directed to a number of pentacene compounds having Structure A above. In some embodiments, the pentacene compounds of the present invention have Structure A above, wherein at least one of R or R' comprises (i) a substituted or unsubstituted cycloalkyl group or (ii) a substituted or unsubstituted cycloalkylalkylene group. In some embodiments, the pentacene compounds have Structure A above, wherein R, R' and R" comprises a combination of (i) one or more branched or unbranched, substituted or unsubstituted alkyl groups, (ii) one or more branched or unbranched, substituted or unsubstituted alkenyl groups, (iii) one or more substituted or unsubstituted cycloalkyl groups, and (iv) one or more substituted or unsubstituted cycloalkylalkylene groups. Further, in some embodiments, the pentacene compounds have Structure A above, wherein R, R' and R" comprises a combination of (i) one or more branched or unbranched, substituted or unsubstituted alkenyl groups, and (iii) one or more substituted or unsubstituted cycloalkyl groups. See, for example, compound LV.

In any of the above-described exemplary pentacene compounds, one or more of R, R' and/or R" may be substituted with one or more substituents. Suitable substituents for the above-described R groups include, but are not limited to, halogens, hydroxyl groups, alkyl groups, cyano groups, amino groups, carbonyl groups, alkoxy groups, thioalkoxy groups, nitro groups, carboxylic acid groups, carboxylic ester groups, alkenyl groups, alkynyl groups, aryl groups, heteroaryl groups, silyl groups (e.g., a trialkylsilyl group with each alkyl group having 1 to 8 carbon atoms), or combinations thereof. Exemplary combinations thereof include halogenated alkyl groups or halogenated alkoxy groups. Typical substituents for alkyl groups and alkenyl groups include, but are not limited to, —F, —OH, —CN, and —COOH. Typical substituents for cycloalkyl groups, cycloalkylalkylene groups, aryl groups, and arylalkylene groups include, but are not limited to, alkyl groups, —F, —OH, —CN, and —COOH.

Further, in any of the above-described exemplary pentacene compounds, the pentacene ring may further comprise one or more of the above-described substituents X. One or more substituents X may be utilized to further tailor a given pentacene compound for a given application. For example, one or more substituents X may be utilized to provide one or more additional benefits including, but not limited to: (1) to further enhance the ability of a given pentacene compound to exhibit two-dimensional stacking; (2) to enhance the compatibility of a given pentacene compound with other similar or dissimilar pentacene compounds or other components when used in a composition (e.g., a particular solvent); and (3) to tune the electronic nature of a given pentacene compound, for example, to change the dominant carrier type from holes to electrons.

As noted above, each X may independently comprise (i) hydrogen, (ii) a halogen, (iii) a branched or unbranched, substituted or unsubstituted alkyl group, (iv) a substituted or unsubstituted aryl group, (v) a branched or unbranched, substituted or unsubstituted alkenyl group, (vi) a branched or unbranched, substituted or unsubstituted alkynyl group, (vii) a substituted or unsubstituted heterocyclic group, (viii) a cyano group, (iv) an ether group, (x) a branched or unbranched, substituted or unsubstituted alkoxy group, or (xi) a nitro group (—$NO_2$). In some embodiments, each X independently comprises (i) hydrogen or (ii) a halogen such as fluorine (—F). In some embodiments, each X independently comprises (i) hydrogen or (ii) a branched or unbranched, substituted or unsubstituted alkyl group such as a fluoroalkyl group (e.g., —$CF_3$). In some embodiments, each X independently comprises (i) hydrogen, (ii) a substituted or unsubstituted aromatic ring structure such as a phenyl group (—C$_6$H$_5$), or (iii) a substituted or unsubstituted heterocyclic group such as a thienyl group (—C$_4$H$_3$S). In some embodiments, each X independently comprises (i) hydrogen or (ii) a nitro group (—NO$_2$).

As further noted above, any two adjacent X groups may combine to form (a) a substituted or unsubstituted carbocyclic ring or (b) a substituted or unsubstituted heterocyclic ring. The carbocyclic or heterocyclic ring is fused to an aromatic ring of the pentacene portion of the compound. The resulting fused carbocyclic ring or heterocyclic ring may be partially saturated or completely saturated. In some embodiments, the only unsaturation is contributed by the aromatic ring that is part of the pentacene portion of the compound. That is, the portion of the resulting fused carbocyclic or heterocyclic ring structure contributed by the two adjacent X groups is saturated. In some embodiments, two adjacent X groups combine to form a substituted or unsubstituted heterocyclic ring containing oxygen within the ring structure (e.g., a dihydrofurano substituent).

In some embodiments, the pentacene compound of the present invention comprises Structure A above, wherein at least one X comprises (i) a halogen, (ii) a branched or unbranched, substituted or unsubstituted alkyl group, (iii) a substituted or unsubstituted aryl group, (iv) a branched or unbranched, substituted or unsubstituted alkenyl group, (v) a branched or unbranched, substituted or unsubstituted alkynyl group, (vi) a substituted or unsubstituted heterocyclic group, (vii) a cyano group, (viii) an ether group, or (ix) a nitro group. In some embodiments, the pentacene compound of the present invention comprises Structure A above, wherein at least one X comprises (i) a fluorine atom, (ii) a fluoroalkyl group, (iii) an aryl group, (iv) a substituted or unsubstituted heterocyclic group, (v) a cyano group, or (vi) a nitro group. In some embodiments, the pentacene compound of the present invention comprises Structure A above, wherein at least one X comprises (i) a fluorine atom, (ii) a trifluoromethyl group, (iii) a phenyl group, or (v) a thienyl group.

A few exemplary structures of compounds of the present invention are provided below:

LXII

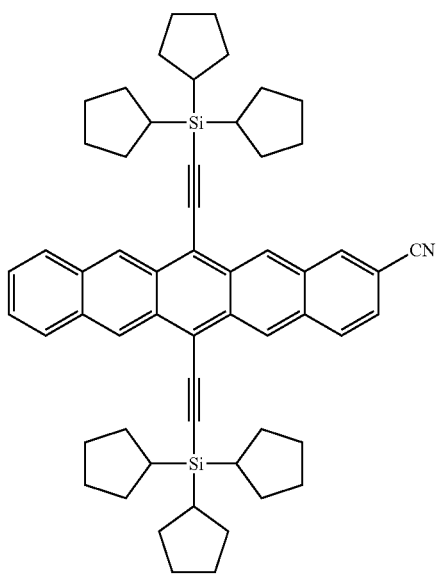

LXIII

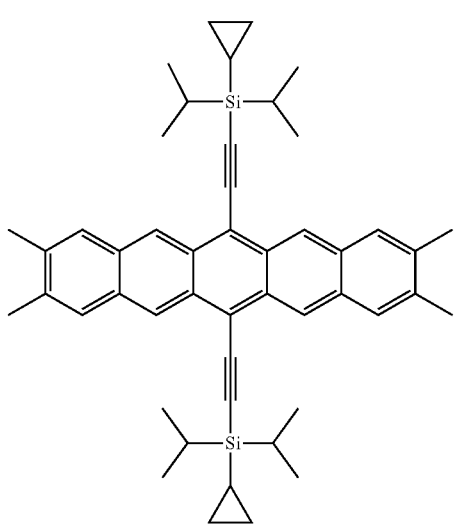

LXI

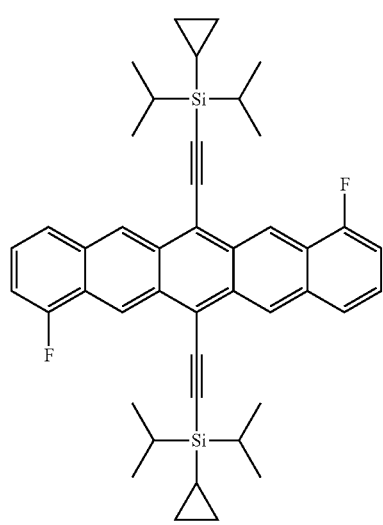

LXIV

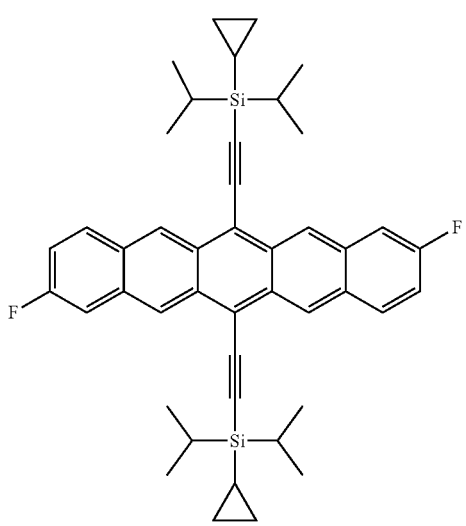

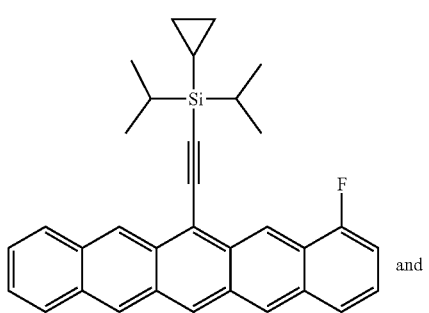

LXV and

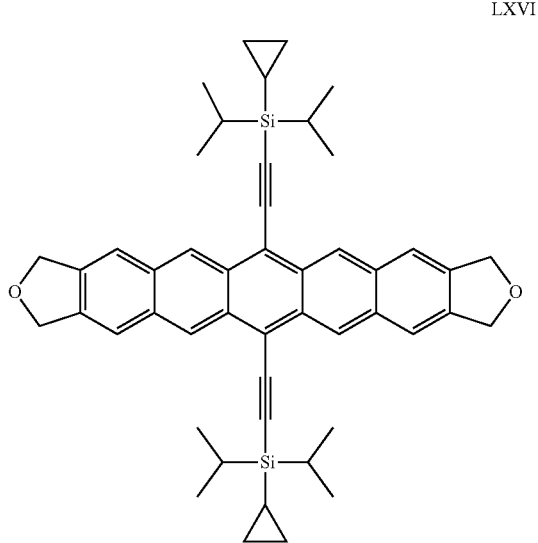

LXVI wherein:
LXI=1,8-difluoro-6,13-Bis[(cyclopropyl, diisopropylsilyl) ethynyl]pentacene (and the 1,11-difluoro isomer);
LXII=2-cyano-6,13-Bis[(tricyclopentylsilyl)ethynyl]pentacene;
LXIII=2,3,9,10-tetramethyl-6,13-Bis[(cyclopropyl, diisopropylsilyl)ethynyl]-pentacene;
LXIV=2,9-Difluoro-6,13-Bis-[(cyclopropyldiisopropylsilyl)ethynyl]pentacene;
LXV=6,13-Bis(cyclopropyl diisopropylsilylethynyl)-1-fluoropentacene; and
LXVI=6,13-Bis(cyclopropyldiisopropylsilylethynyl)-2,3:9, 10-bis(c-dihydrofur-ano)pentacene.

As discussed above, when used in applications such as electrical devices (e.g., transistors), the pentacene compounds desirably enable the formation of a semiconductor layer having a maximum charge carrier mobility value greater than or equal to 2.0 cm$^2$/V-s. More desirably, the pentacene compounds enable the formation of a semiconductor layer having a maximum charge carrier mobility value greater than or equal to 2.0 cm$^2$/V-s as measured by the Mobility Value Test Method I, the Mobility Value Test Method II, and/or the TF&CCMV Test Method, each of which are described below in the Test Method section of the examples.

The present invention is further directed to compositions comprising (I) one or more of the above-described pentacene compounds, and (II) a solvent. Typical solvents suitable for forming compositions of the present invention include, but are not limited to, organic solvents such as ketones, aromatic hydrocarbons, and the like. Suitable solvents include, but are not limited to, toluene, ethylbenzene, butylbenzene, chlorobenzene, dichlorobenzene, tetrahydrofuran, isophorone, anisole, tetrahydronaphthalene, and cyclohexanone. In one exemplary embodiment, the composition comprises one or more of the above-described pentacene compounds, and a solvent such as toluene, butylbenzene, anisole or cyclohexanone.

Typically, one or more of the above-described pentacene compounds are present in a given composition at a concentration of at least 0.1 wt % based on a total weight of the composition. As discussed above, in some embodiments, the pentacene compound used to form a given composition is soluble in a given solvent, such as toluene, at a concentration of up to about 21 wt % (or greater than 21 wt %). Although a given pentacene compound may have a solubility in a given organic solvent of as much as 21 wt % or greater, typical compositions of the present invention comprise one or the above-described pentacene compounds at a concentration ranging from about 0.1 wt % to about 5.0 wt %, more typically, from about 1.5 wt % to about 3.0 wt %.

In some embodiments, compositions of the present invention comprise at least one of the above-described pentacene compounds and a solvent. In other embodiments, compositions of the present invention comprise at least one of the above-described pentacene compounds and a solvent in combination with one or more additional composition components. When present, suitable additional composition components include, but are not limited to, a polymer additive, a rheological modifier, or a combination thereof. In some exemplary embodiments, the compositions comprise a polymer additive selected from the group consisting of polystyrene, poly(alpha-methylstyrene), poly(methyl methacrylate), poly(4-cyanomethyl styrene), poly(4-vinylphenol), or any other suitable polymer disclosed in U.S. Patent Publication No. 2004/0222412 A1 or U.S. Patent Publication No. 2007/0146426 A1, the subject matter of both of which is hereby incorporated by reference in its entirety. In some desired embodiments, the polymer additive comprises polystyrene, poly(alpha-methylstyrene) or polyvinylphenol.

When present, each additional composition component (i.e., components other than the pentacene compound) is independently present in an amount of greater than 0 to about 50 wt % based on a total weight of the composition. Typically, each additional composition component (i.e., components other than the pentacene compound) is independently present in an amount ranging from about 1.0 to about 10.0 wt % based on a total weight of the composition. For example, when a polymer additive (e.g., polystyrene) is present in the composition, the polymer additive is typically present in an amount of greater than 0 to about 5.0 wt %, more typically, from about 0.5 to about 3.0 wt % based on a total weight of the composition.

In some embodiments, the resulting composition desirably has composition properties (e.g., composition stability, viscosity, etc.) that enable the composition to be coated onto a substrate via conventional coating processes. Suitable conventional coating processes include, but are not limited to, spin coating, knife-coating, roll-to-roll web-coating, and dip coating, as well as printing processes such as ink-jet printing, screen printing, and offset lithography. In one desired embodiment, the resulting composition is a printable composition, even more desirably, an ink jet printable composition.

The above-described compositions may be coated onto a substrate. The resulting substrate has at least one coatable surface and a coated layer on the at least one coatable surface, wherein the coated layer comprises a pentacene compound having Structure A, wherein R, R', R", x, y, z and X are as described above. As discussed above, the coated layer may further comprise one or more additional composition components other than at least one of the above-described pentacene compounds.

The compositions of the present invention may be coated onto a variety of substrates. Suitable substrates include, but are not limited to, polymeric films such as polyethylene terephthalate (PET), polyethylene naphthalate (PEN), and polyimides, and inorganic substrates such as silica, alumina, silicon wafers, and glass. In one exemplary embodiment, the substrate comprises an electronic device or an electronic device component. For example, compositions of the present invention may be coated onto a substrate so as to form a semiconductor layer of an electronic device such as a thin film transistor (TFT) or an organic light-emitting diode (OLED). Compositions of the present invention may be coated onto a substrate so as to form a photovoltaic module or solar cell therein, or a sensor.

The above described pentacene compounds and compositions made therefrom enable the formation of electronic devices (e.g., transistors) having a charge carrier mobility value greater than 2.0 $cm^2/V$-s. In one exemplary embodiment, the electronic device comprises a coated layer, wherein the coated layer comprises a pentacene compound having Structure A, wherein R, R', R", x, y and z are as described above. The resulting electronic device has a charge carrier mobility value greater than 2.0 (or greater than about 2.1, or greater than about 2.2, or greater than about 2.3, or greater than about 2.4, or greater than about 2.5, or greater than about 2.6, or greater than about 2.7, or greater than about 2.8, or greater than about 2.9, or greater than about 3.0, or greater than about 3.1, or greater than about 3.2, or greater than about 3.3, or greater than about 3.4, or greater than about 3.5) $cm^2/V$-s as measured using the disclosed Mobility Value Test Method I and/or the disclosed Mobility Value Test Method II and/or the disclosed TF&CCMV Test Method and/or similar methods for measuring the charge carrier mobility value of an electronic device.

Exemplary electronic devices of the present invention may have a top contact/bottom gate TFT construction as shown in FIG. 1. As shown in FIG. 1, exemplary electronic device 10 comprises substrate 11, gate electrode 16, dielectric layer 12, semiconductor layer 13, source electrode 14, and drain electrode 15. Materials for forming substrate 11, gate electrode 16, dielectric layer 12, source electrode 14, and drain electrode 15 of exemplary electronic device 10 may comprise any materials typically used to form TFT electronic devices.

Suitable materials for forming substrate 11 include, but are not limited to, glass, polyethylene terephthalate, polyethylene naphthalate, and polyimide. Suitable materials for forming dielectric layer 12 include, but are not limited to, any of a variety of polymers such as poly(4-vinylphenol), poly(methylmethacrylate), and poly(4-cyanomethylstyrene), which are typically deposited from solution, but may also be formed in place via curing of a formulation containing functional monomers and/or oligomers and a curing agent. The dielectric layer 12 may further include inorganic fillers such as, but not limited to, $BaTiO_3$, $SiO_2$, $ZrO_2$, which act to enhance the dielectric constant of dielectric layer 12.

Suitable materials for forming semiconductor layer 13 comprise the above-described compositions of the present invention. Suitable materials for forming each of gate electrode 16, source electrode 14 and drain electrode 15 include, but are not limited to, carbon nanotubes, poly(3,4-ethylenedioxythiophene) (PEDOT), polyaniline (PANT), gold, silver, aluminum, copper, titanium, palladium, platinum, chromium, as well as blends thereof (e.g., blends, alloys, multi-layer composites of the various electrode materials).

In some cases, the substrate 11, the gate electrode 16, and the dielectric layer 12 are heavily-doped n-type silicon wafers with thermal oxide (such as those commercially available from Noel Technologies, Inc. (Campbell, Calif.)), wherein the heavily-doped n-type silicon wafer serves as both the substrate and gate electrode, and the thermal oxide serves as the dielectric layer.

In some exemplary embodiments, one or more of the following layers are printable (e.g., ink jet printable) layers: gate electrode 16, dielectric layer 12, semiconductor layer 13, source electrode 14, and drain electrode 15. For example, suitable printable compositions for forming dielectric layer 12, semiconductor layer 13, gate electrode 16, source electrode 14, and drain electrode 15 are disclosed in U.S. Patent Application Publication No. 20070114516 A1, now U.S. Pat. No. 7,498,662, the subject of which is incorporated herein by reference in its entirety.

Electronic devices of the present invention desirably comprise at least one of the above-mentioned pentacene compounds and have a charge carrier mobility value greater than 2.0 $cm^2/V$-s. Such electronic devices may comprise, for example, the following specific top contact/bottom gate TFT construction as shown in exemplary device 20 of FIG. 2: a gate electrode layer 16 comprising a heavily n-doped silicon wafer with a first dielectric layer 12a in the form of a thermal oxide ($SiO_2$) layer positioned over the gate electrode layer 16 (e.g., a heavily n-doped silicon wafer commercially available from Noel Technologies, Inc. (Campbell, Calif.)); a second dielectric layer 12b comprising a polymeric dielectric composition comprising SARTOMER™ SR-368 (Sartomer Company Inc. (Exton, Pa.)) (about 8.5 wt %), zirconia nanoparticles surface treated with gamma-methacryloxypropyltrimethoxysilane (SILQUEST® A-174 silane from OSi Specialties (South Charleston, W. Va.)) and formed as disclosed in U.S. patent application Ser. Nos. 11/771,787 and 11/771,859 (see, for example, "Preparatory Example 1—Dielectric Ink" in each application), the subject matter of which is hereby incorporated by reference in its entirety (about 40.0 wt %), IRGACURE™ 184 photoinitiator (Ciba Corporation (Newport, Del.)) (about 1.5 wt %), and isophorone (Sigma-Aldrich (Milwaukee, Wis.)) (about 50.0 wt %); a semiconductor layer 13 comprising at least one of the above-described pentacene compounds (e.g., one of compounds I, II or IV) (about 2.0 wt %), polystyrene (Polymer Source Inc. (Montreal, Canada)) (about 1.0 wt %), and butylbenzene (Sigma-Aldrich (Milwaukee, Wis.)) (about 97.0 wt %); a source electrode 14 comprising gold; and a drain electrode 15 comprising gold.

The above-described pentacene compounds of the present invention may be prepared by a method comprising the steps of forming a substituted silyl acetylene having a desired combination of R, R' and R" substituents, and then reacting the substituted silyl acetylene with 6,13-pentacenequinone. The step of forming a substituted silyl acetylene having a desired combination of R, R' and R" substituents may comprise a number of process steps including, but not limited to, a first substitution reaction wherein one or more first substituents bonded to the silicon atom of a given silyl acetylene (e.g., a trimethylsilyl acetylene) are replaced with one or more second substituents (e.g., an isopropyl group); and a second substitution reaction wherein one or more of the second substituents bonded to the silicon atom are replaced with one or more third substituents (e.g., an isopropenyl group).

The methods of forming pentacene compounds of the present invention may further comprise one or more of the following method steps: purification by at least one and, in some cases, two or three recrystallization steps from a suitable solvent such as acetone, wherein the pentacene compound is dissolved in an amount of boiling acetone, which dissolves all solids and is then cooled to about 0-4° C. while protecting the solution from light to prevent photodegradation. The solids are then collected by filtration and dried in vacuum to remove residual acetone.

Once formed, pentacene compounds of the present invention may be combined with a solvent and one or more additional components to form compositions, such as printable compositions. As discussed above, pentacene compounds of the present invention (e.g., compounds I to LIV) may be incorporated into at least one of the above-referenced organic solvents (e.g., toluene) to form a first composition comprising up to or greater than 21 wt % of the pentacene compound. Additional composition components such as those described above (e.g., polystyrene) may be incorporated into the first composition to provide a final composition. Desirably, the final composition is printable via an ink jet printing apparatus.

The compositions of the present invention (e.g., the first composition, the final composition, or both) containing at least one of the above-described pentacene compounds of the present invention may be used to form a variety of coatings, substrates having a coated layer thereon, electronic device components, and electronic devices. Desirably, the resulting coating, substrate having a coated layer thereon, electronic device component, or electronic device comprises a pentacene compound having Structure A, wherein R, R', R", x, y, z and X are as described above. More desirably, the resulting coating, substrate having a coated layer thereon, electronic device component, or electronic device comprises a pentacene compound having Structure A, wherein R, R' and R" together comprise two sterically similar groups and one sterically dissimilar group, the two sterically similar groups being oriented on opposite sides of a plane extending though the five ring structure of the pentacene compound, and the sterically dissimilar group being substantially within the plane extending though the five ring structure of the pentacene compound. In some desired embodiments, the resulting coating, substrate having a coated layer thereon, electronic device component, or electronic device comprises a pentacene compound having Structure A, wherein z=0, R comprise isopropyl, and R' comprises isopropenyl. In other desired embodiments, the resulting coating, substrate having a coated layer thereon, electronic device component, or electronic device comprises one of pentacene compounds I, II and IV shown above.

The present invention is described above and further illustrated below by way of examples, which are not to be construed in any way as imposing limitations upon the scope of the invention. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

These examples are merely for illustrative purposes only and are not meant to be limiting on the scope of the appended claims. All parts, percentages, ratios, etc. in the examples and the rest of the specification are by weight unless indicated otherwise.

TABLE 4

Materials Used in Examples

| Material | Abbreviation (if any) | Source |
|---|---|---|
| 2-bromopropene | | Sigma-Aldrich |
| Ammonium chloride | $NH_4Cl$ | (Milwaukee, WI) |
| 2,2'-Azobis(2-methylpropionitrile) | | |
| Benzoquinone | | |
| Bromocyclopropane | | |
| N-butylbenzene | | |
| N-butyllithium | n-BuLi | |
| Chlorobenzene | | |
| Chlorodiisopropylsilane | | |
| Cyclohexane-1,4-dione | | |
| Cyclopropylmagnesium bromide | | |
| Decane | | |
| Dichlorodiisopropylsilane | | |
| Dichloroethane | | |
| Dichloromethane | DCM | |
| Diethyl ether | | |
| Dimethylformamide | DMF | |
| Ethanol | EtOH | |
| Ethylbenzene | | |
| Ethylmagnesium chloride | | |
| Ethynylmagnesium bromide | | |
| Allyl magnesium bromide | | |
| Hexamethyl disilazane | HMDS | |
| Heptane | | |
| Hexane | | |
| Hydrochloric acid | HCl | |
| Isophorone | | |
| Isopropyllithium | | |
| Magnesium sulfate | $MgSO_4$ | |
| Methanol | MeOH | |
| 2-Methyl-1,3-dithiane | | |
| 4-Methoxythiophenol | | |
| N-Bromosuccinimide | NBS | |
| Pentane | | |
| Potassium iodide | KI | |
| 6,13-Pentacenequinone | | |
| Pentachlorothiophenol | | |
| Pentafluorothiophenol | | |
| Stannous chloride dihydrate | $SnCl_2 \cdot 2H_2O$ | |
| Tetrahydrofuran (anhydrous) | THF | |
| Thiophenol | | |
| Toluene | | |
| (3-Heptafluoroisopropoxy)propyl-trichlorosilane | | Gelest (Morrisville, PA) |
| Decanedithiol | | Alfa Aesar |
| 1,4-Anthraquinone | | (Ward Hill, MA) |
| 3-Fluoro-o-xylene | | |
| 4-Fluoro-o-xylene | | |
| 2-Bromo-1-butene | | |
| Trimethylsilyl acetylene | | |
| Dodecanethiol | | |
| Octanethiol | | |
| n-doped silicon wafers (heavily doped) | | Noel Technologies, Inc. (Campbell, CA) |
| n-doped silicon wafers with thermal oxide | | |
| Polystyrene (118K MW) | | Polymer Source Inc. (Montreal, Canada) |
| SARTOMER ™ SR-368 | | Sartomer Company Inc. (Exton, PA) |
| Ink jet printable silver ink Cabot AG-IJ-G-100-S1 | | Cabot Corporation (Alburquerque, NM) |
| IRGACURE ™ 184 photoinitiator | | Ciba Corporation (Newport, DE) |

TABLE 4-continued

Materials Used in Examples

| Material | Abbreviation (if any) | Source |
|---|---|---|
| zirconia nanoparticles surface treated with silane A-174[1] | | 3M Company (St. Paul, MN) |

[1] The method of forming zirconia nanoparticles surface treated with silane A-174 as used in the present invention is disclosed in U.S. patent applications Nos. 11/771,787 and 11/771,859 (see, for example, "Preparatory Example 1 - Dielectric Ink" in each application), both of which were filed on and assigned to The 3M Company (St. Paul, MN), the subject matter of both of which is incorporated herein by reference in its entirety.

Figure 3:
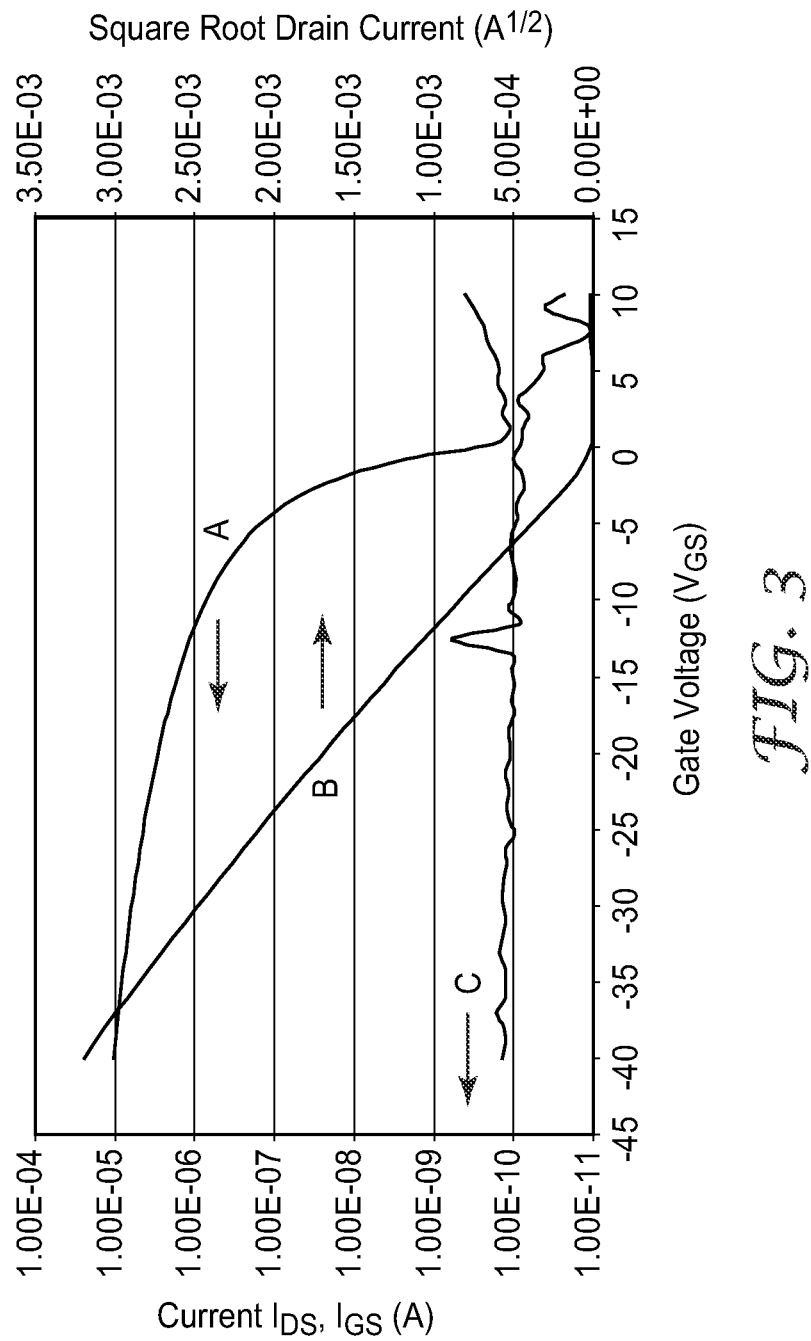
FIG. 3 is a representative plot of transistor outputs ($I_{DS}$ and $(I_{DS})^{1/2}$) as a function of sweeping gate bias.

Test Methods:

Mobility Value Test Method I:

Once formed, a transistor's performance characteristics are measured in air under ambient lighting using two Source Measure Units (Model 2400 from Keithley Instruments, Inc. (Cleveland, Ohio)). The devices were placed on a SIGNATONE™ 1160 Series probe station and probes connected using SIGNATONE™ S-725-PRM manipulators (Signatone Corp. (Gilroy, Calif.)). The drain to source bias voltage ($V_{Ds}$) was held at −40 V, while the gate to source bias ($V_{GS}$) was incremented over the range +10 V to −40 V in 1 V steps. FIG. 3 graphically displays exemplary measured parameters.

In FIG. 3, traces labeled "A" indicate measured drain current ($I_{DS}$) as a function of $V_{GS}$. Traces labeled "B" indicate the square root of measured drain current ($I_{DS}$) versus $V_{GS}$, and traces labeled "C" indicate measured gate current ($I_{GS}$) versus $V_{GS}$. The saturated field effect mobility ($\mu$) can be calculated from the slope (m) of the square root of drain current versus $V_{GS}$ (trace "B") using the following equation:

$$\mu = 2\left(\frac{m^2 L}{W C_i}\right)$$

where $C_i$ is the specific capacitance of the gate dielectric, W is the channel width, and L is the channel length. The charge carrier mobility value reported is the maximum charge carrier mobility value observed over the range of measurement.

Using the square root of $I_{DS}$ versus $V_{GS}$ curve (trace "B"), the X-axis extrapolation of a straight-line fit was taken as the threshold voltage ($V_t$). The on/off ratio was taken as the difference between the minimum and maximum drain current ($I_{DS}$) values of the $I_{DS}$-$V_{GS}$ curve.

Mobility Value Test Method II:

Once formed, a transistor's performance characteristics are measured at room temperature in air using a Semiconductor Parameter Analyzer (Model 4200 from Keithley Instruments, Inc., Cleveland, Ohio)). The square root of the drain-source current ($I_{DS}$) was plotted as a function of gate-source bias ($V_{GS}$) from +10 V to −40 V for a constant drain-source bias ($V_{Ds}$) of −40 V. Using the equation:

$$I_{DS} = \mu C \times W/L \times (V_{GS} - V_t)^2/2,$$

the saturation field effect mobility ($\mu$) was calculated from the linear portion of the curve using the specific capacitance of the gate dielectric (C), the channel width (W) and the channel length (L). Threshold voltage, sub-threshold slope, and on/off ratio were determined as in Method I.

Transistor Fabrication & Charge Carrier Mobility Value Test Method (i.e., the TF&CCMV Test Method):

A transistor is formed using the specific materials and process steps as outlined in Example 4 below. Once formed, the transistor's charge carrier mobility value was measured using Mobility Value Test Method I described above.

Thermal Analysis Test Method

A TA Instrument (New Castle, Del.) Model Q200 DSC with an autosampler was used in the characterization. 2 to 10 milligrams of the material to be characterized were placed in an aluminum pan (Standard or Tzero™ available from TA Instruments) and a lid was crimped according to the requirements of the specific pan used. The pan was placed in the autosampler for automatic loading into the DSC sample cell. An empty pan of the same type was used as the reference.

An initial scan was conducted wherein the sample was cooled to 0° C. and then the temperature was increased at a controlled rate (5° C./min.) to 320° C. This scan revealed the presence of the endothermic and exothermic events. The temperatures at which these events occurred were used to determine the temperature limits of the second scan, which determined if the lower temperature transitions were reversible.

A second scan was conducted using a newly prepared sample wherein the temperature was ramped to a temperature about 10° C. above the highest temperature endotherm associated with a solid-solid transition while staying below the temperature at which the melt and subsequent Diels-Alder reaction occurred. The temperature was then decreased at a controlled rate (5° C./min.) to a temperature below the lowest temperature thermal event and then once again increased at 5° C./min. to beyond the temperature at which the material underwent irreversible transformation (Diels-Alder reaction).

The events present in the thermogram were analyzed using the "Integrate Peak Linear" or "Onset Point" functions of the Analyze menu in the Universal Analysis software provided with the instrument to determine the temperature at which the event occurred and, if the specimen was accurately weighed, the enthalpy associated with the transition.

Figure 4:
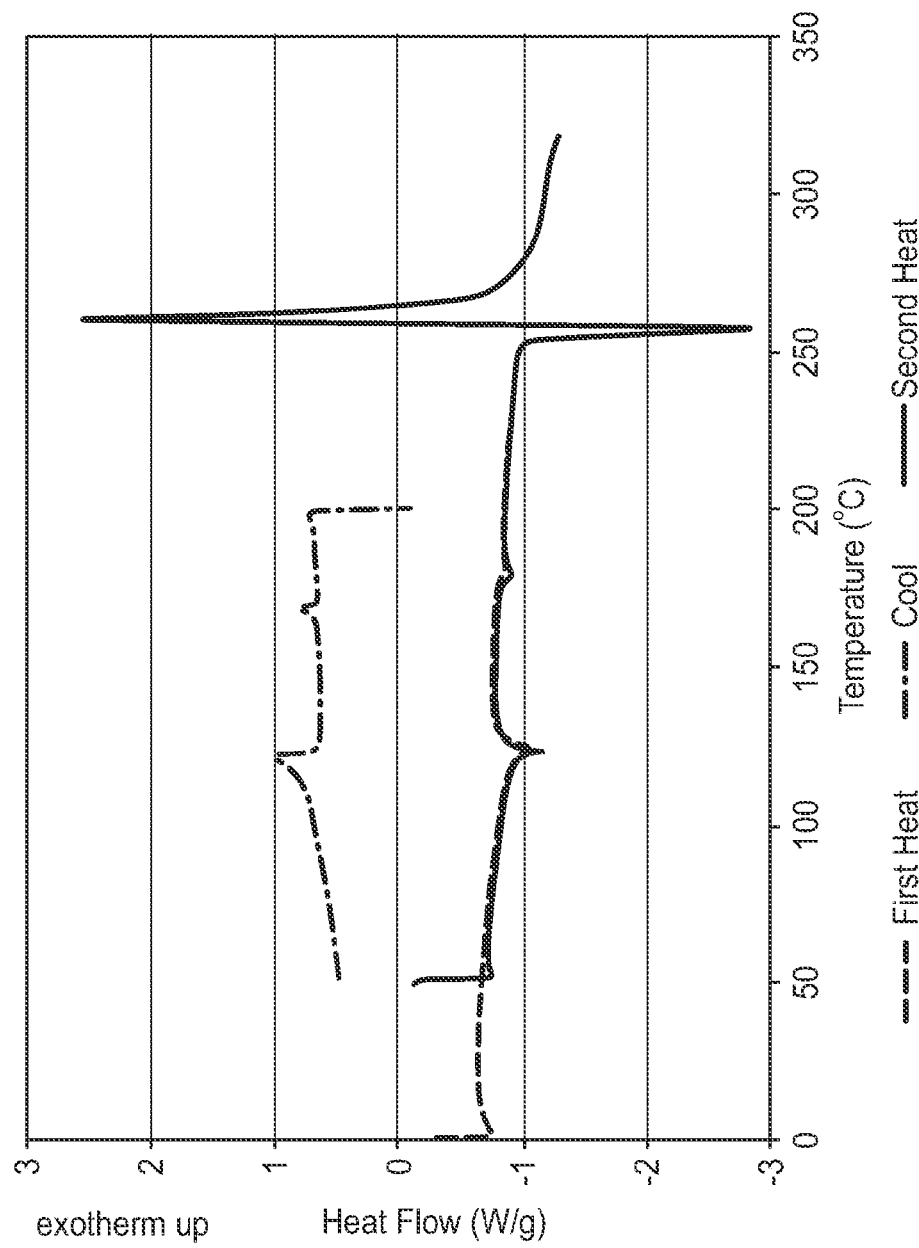
FIG. 4 is a representative thermogram of a Differential Scanning Calorimetry graph for TIPS-pentacene showing the thermal transitions.

A representative thermogram of the second scan of TIPS Pentacene is shown in FIG. 4, which reveals that the event occurring at ~124° C. is reversible as is the event present at ~180° C. At ~266° C. there is evidence of the onset of an endotherm followed by a significant exotherm. Observations of TIPS Pentacene on a Fisher-John melting point apparatus confirmed that the two lower thermal events are solid-solid transitions and the material indeed melts (solid-liquid transition) at ~266° C. The results of thermal analysis for pentacene compounds of the present invention are show in Table 8 below.

Example 1

Synthesis of 6,13-Bis(allyldiisopropylsilylethynyl)pentacene (Allyl DIPS)

Synthesis of Allyldiisopropylsilyl Acetylene

Dichlorodiisopropylsilane (4.00 g, 21.6 mmol) and anhydrous THF (20 mL) were added into a dry 250-mL round bottom flask equipped with a stir bar. The flask was equipped with a dry condenser. Allyl magnesium bromide (22.0 mL, 22.0 mmol, 1.0 M in THF) was added to the flask through the condenser to form a first mixture. The first mixture was heated to 63° C. for 12 hours, and then cooled to room temperature.

Trimethylsilyl acetylene (2.36 g, 24.0 mmol) and anhydrous THF (12 mL) were added to a separate dry 100-mL round bottom flask equipped with a stir bar. The 100-mL flask reaction mixture was cooled to 0° C., and n-butyllithium (9.2 mL, 23 mmol, 2.5 M in hexane) was added dropwise, followed by stirring for 90 minutes to form a second mixture.

The 250-mL reaction mixture (i.e., the first mixture) was then cooled to 0° C., and the second mixture was added dropwise via syringe. The combined mixture was allowed to stir overnight. The combined mixture was then poured into 100 mL saturated $NH_4Cl$ solution, and rinsed with a 1:1 hexane:diethyl ether mixture (100 mL). The organic layer was separated, and the water layer was extracted again with 50 mL of 1:1 hexane:diethyl ether mixture (100 mL). The organic portions were combined, washed with water (50 mL) and brine (25 mL), then dried over $MgSO_4$, filtered, and concentrated via rotary evaporation.

The product was taken up in THF (50 mL), and MeOH saturated with $K_2CO_3$ (100 mL) was added, followed by stirring for 2 hours. Water (50 mL) and hexane (100 mL) were added, and the organic layer was separated. The water layer was extracted again (20 mL hexane) and the organic layers were combined. The combined organic layers were washed with water (20 mL), dried over $MgSO_4$ and filtered, followed by solvent evaporation. The product was purified by column chromatography (5:1 hexane:DCM), yielding 1.7 g of a colorless oil (9.4 mmol, 44%). Analysis of the product provided the following data: $^1$H-NMR (200 MHz, $CDCl_3$) δ=5.87 (m, 1H), 4.94 (m, 2H), 2.39 (s, 1H), 1.70 (dt, J=1.4 Hz, 8 Hz, 2H), 1.08 (s, 14H).

Synthesis of
6,13-Bis(allyldiisopropylsilylethynyl)pentacene
(Allyl DIPS)

The above allyldiisopropylsilyl acetylene (1.62 g, 9.36 mmol) and anhydrous THF (20 mL) were added to a dry 100-mL round bottom flask with a stir bar and cooled to 0° C. n-Butyllithium (3.1 mL, 7.8 mmol, 2.5 M in hexane) was added dropwise and the solution was allowed to warm over 1 hr. 6,13-Pentacenequinone (1.22 g, 3.89 mmol) was added and the mixture was stirred for 48 hr. The reaction was quenched by the addition of 0.5 mL of saturated $NH_4Cl$ solution, then diluted with MeOH (60 mL) to form a reaction mixture.

In a large Erlenmeyer flask, MeOH (600 mL), $SnCl_2.2H_2O$ (2.60 g, 11.5 mmol), and 25% HCl (2.5 mL) were combined with stirring and cooled to 0° C. to form a second solution. The reaction mixture was added in a slow stream to the second solution and rinsed in with additional MeOH. Additional 25% HCl (3 mL) was added, and the mixture was stirred for 20 minutes, then placed in the refrigerator for 1 hr. The mixture was filtered to yield 1.3 g of a greenish-blue solid. The resulting solid was dissolved in minimal DCM (~5 mL), then diluted with hexane (200 mL) and rinsed onto a thick plug. Excess acetylene was removed by flushing the plug with hexane. The product was eluted using 5:1 hexane:DCM. The solvent was removed to yield 0.5 g of blue solid. The solid was dissolved in hot acetone, then filtered while hot to remove a green impurity, and allowed to crystallize overnight. A second recrystallization from acetone yielded 0.38 g of blue needles (0.62 mmol, 16%). Analysis of the blue needles product provided the following data: $^1$H-NMR (200 MHz, $CDCl_3$) δ=9.3 (s, 4H), 8.0 (dd, J=3.4 Hz, 4H), 7.4 (dd, J=3.4 Hz, 4H), 6.38 (m, 2H), 5.1 (m, 4H), 2.0 (m, 4H), 1.3-1.4 (m, 28H).

Example 2

Synthesis of 6,13-Bis(isopropenyldiisopropylsilyl-ethynyl)pentacene (IP-DIPS)

Synthesis of Isopropenyldiisopropylsilyl Acetylene

2-Bromopropene (4.32 g, 38.6 mmol) and anhydrous THF (20 mL) were combined in a dry 250-mL round-bottom flask with a stir bar, and then cooled to −78° C. n-Butyllithium (14.8 mL, 37 mmol, 2.5 M in hexanes) was added dropwise. Stirring was continued and the temperature was maintained for 10 minutes, followed by the dropwise addition of dichlorodiisopropylsilane (6.85 g, 37.0 mmol). The mixture was allowed to warm and stirred for 48 hr to form a first mixture.

In a separate dry 100-mL round-bottom flask with a stir bar, trimethylsilylacetylene (3.93 g, 40.0 mmol) and anhydrous THF (10 mL) were combined and cooled to 0° C. n-Butyllithium (14.8 mL, 37 mmol, 2.5 M in hexane) was added dropwise and stirring was continued for 2 hr to form a second mixture. The first reaction mixture was cooled to 0° C. The second mixture was added to the first mixture by syringe, and stirring was continued for 12 hr. The reaction flask was emptied into a saturated $NH_4Cl$ solution (100 mL), and then a 1:1 hexane:diethyl ether mixture (100 mL) was added. The organic layer was separated, and the water layer was extracted again with the 1:1 hexane:diethyl ether mixture (20 mL). The organic portions were combined, washed with water (20 mL) and brine (20 mL), then dried over $MgSO_4$, filtered, and concentrated via rotary evaporation.

The product mixture was dissolved in THF (50 mL), then MeOH saturated with $K_2CO_3$ was added, and stirring was continued for 2 hr. Water (100 mL) and hexane (100 mL) were added, and the organic layer was separated, then washed with water (20 mL), dried over $MgSO_4$, filtered, and concentrated via rotary evaporation to yield 4.6 g of a colorless oil (26 mmol, 70%). Analysis of the colorless oil product provided the following data: $^1$H-NMR (200 MHz, $CDCl_3$) δ=5.76 (m, 1H), 5.51 (m, 1H), 2.42 (s, 1H), 1.88 (s, 3H), 1.05 (m, 14H).

Synthesis of 6,13-Bis(isopropenyldiisopropylsilyl-ethynyl)pentacene (IP-DIPS)

The above isopropenyldiisopropylsilyl acetylene (3.00 g, 16.7 mmol) and anhydrous THF (16 mL) were combined in a dry 100-mL round bottom flask with a stir bar. After cooling the flask to 0° C., n-butyllithium (5.6 mL, 14 mmol, 2.5 M in hexane) was added dropwise and stirring was continued for 2 hr. 6,13-Pentacenequinone (1.4 g, 4.6 mmol) was added and the mixture was stirred for 48 hr. The reaction was quenched by the addition of 0.5 mL of saturated $NH_4Cl$ solution, and then diluted with MeOH (50 mL) to form a first reaction mixture.

In a large Erlenmeyer, $SnCl_2.2H_2O$ (5.8 g, 25 mmol) was dissolved in MeOH (800 mL) and 25% HCl (5 mL) was added to form a second mixture. After cooling the second mixture to 0° C., the first reaction mixture was added in a slow stream and allowed to stir for 20 minutes, and then placed in the refrigerator for 1 hr. The mixture was filtered to yield a blue-green solid that was taken up in minimal DCM (~5 mL), diluted with hexane (200 mL), and then rinsed onto a thick silica plug. Excess acetylene was flushed using hexane, and then the product was eluted using a 5:1 hexane:DCM mixture. Removal of solvent yielded 1.35 g of a blue solid. Recrystallization from acetone (~400 mL) yielded 1.1 g of blue needles (1.74 mmol, 38%). Analysis of the blue needles product provided the following data: $^1$H-NMR (200 MHz, $CDCl_3$) δ=9.3 (s, 4H), 8.0 (dd, J=3.2 Hz, 4H), 7.4 (dd, J=3.2 Hz, 4H), 5.9 (bm, 2H), 5.8 (bm, 2H), 2.1 (s, 6H), 1.3-1.4 (m, 28H); and MS (70 eV, EI) m/z 634 (100%, $M^+$).

Example 3

6,13-Bis(diisopropenylisopropylsilylethynyl)pentacene (DIIP-IPS)

Synthesis of Diisopropenylisopropylsilyl Acetylene

2-Bromopropene (14.5 g, 120 mmol) and anhydrous THF (100 mL) were combined in a dry 500-mL round-bottom flask with a stir bar, and then cooled to −78° C. n-Butyllithium (47.5 mL, 119 mmol, 2.5 M in hexane) was added dropwise. Stirring was continued and the temperature was maintained for 10 minutes, followed by the dropwise addition of trichloroisopropylsilane (10.5 g, 59.4 mmol). The mixture was allowed to warm and was stirred for 48 hr to form a first reaction mixture.

In a separate dry 250-mL round-bottom flask with a stir bar, trimethylsilylacetylene (7.37 g, 75.0 mmol) and anhydrous THF (20 mL) were combined and cooled to 0° C. n-Butyllithium (28 mL, 70 mmol, 2.5 M in hexane) was added dropwise and stirring was continued for 2 hr to form a second reaction mixture. The first reaction mixture was cooled to 0° C., then the second reaction mixture was added by syringe, and stirring was continued for 12 hr. The reaction flask was emptied into a saturated $NH_4Cl$ solution (100 mL), then a 1:1 hexane:diethyl ether mixture (100 mL) was added. The organic layer was separated, and the water layer was extracted again with the 1:1 hexane:diethyl ether mixture (20 mL). The organic portions were combined, washed with water (20 mL) and brine (20 mL), then dried over $MgSO_4$, filtered, and concentrated via rotary evaporation.

The product mixture was dissolved in THF (50 mL), then MeOH saturated with $K_2CO_3$ was added, and stirring was continued for 2 hr. Water (100 mL) and hexane (100 mL) were added, and the organic layer was separated, washed with water (20 mL), dried over $MgSO_4$, filtered, and concentrated via rotary evaporation to yield 2.1 g of a colorless oil (11.8 mmol, 20%). Analysis of the colorless oil product provided the following data: $^1$H-NMR (200 MHz, $CDCl_3$) δ=5.76 (m, 2H), 5.55 (m, 2H), 2.48 (s, 1H), 1.88 (m, 6H), 1.05 (m, 7H).

Synthesis of 6,13-Bis(diisopropenylisopropylsilylethynyl)pentacene (DIIP-IPS)

The above diisopropenylisopropylsilyl acetylene (1.00 g, 5.59 mmol) and anhydrous THF (10 mL) were combined in a dry 100-mL round bottom flask with a stir bar. After cooling the flask to 0° C., n-butyllithium (2.1 mL, 5.3 mmol, 2.5 M in hexane) was added dropwise and stirring was continued for 2 hr. 6,13-Pentacenequinone (0.79 g, 2.5 mmol) was added and the mixture was stirred for 48 hr. The reaction was quenched by the addition of 0.5 mL of saturated $NH_4Cl$ solution, and purged with $N_2$. $SnCl_2.2H_2O$ (2.26 g, 10.0 mmol) and HI (5-6 drops) were added and the reaction was stirred under $N_2$ for 20 min. Hexane (50 mL) and water (20 mL) were added and the mixture was filtered through CELITE® 545 filtration material from Mallinckrodt Baker, Inc. (Phillipsburg, N.J.).

The organic layer was separated, washed with water, dried over $MgSO_4$, filtered and concentrated via rotary evaporation to yield a blue-green solid. The product was taken up in minimal DCM (~5 mL), diluted with hexane (200 mL), and then rinsed onto a thick silica plug. Excess acetylene was flushed using hexane. The product was then eluted using a 9:1 hexane:DCM mixture. Removal of solvent yielded 0.13 g of a blue solid. Recrystallization from acetone (~10 mL) yielded 30 mg of small blue needles (0.048 mmol, 2%). Analysis of the blue needles product provided the following data: $^1$H-NMR (200 MHz, $CDCl_3$) δ=9.3 (s, 4H), 8.0 (dd, J=3.2 Hz, 4H), 7.4 (dd, J=3.2 Hz, 4H), 5.9 (m, 4H), 5.8 (m, 4H), 2.1 (t, J=1.4 Hz, 12H), 1.3-1.4 (m, 14H); and MS (70 eV, EI) m/z 630 (100%, M+).

Example 4

Preparation of Electronic Device with Au Top Contacts

An n-type silicon wafer with thermal oxide (i.e., silicon <100> wafer highly doped n+ (arsenic) with a resistivity of <0.005 ohm-cm, and supplied with a 1000 Å thermal oxide ($SiO_2$) on the front surface and coated with 100 Å TiN and 5000 Å aluminum on the back surface from Noel Technologies, Inc. (Campbell, Calif.)) was (i) washed with acetone and dried with $N_2$, (ii) washed with isopropyl alcohol (IPA) and dried with $N_2$, (iii) washed with deionized water (DI) water and dried with $N_2$, and (iv) then treated with $UV/O_3$ for 10 minutes. The wafer sample was then (i) coated with a ZrOAc solution having a viscosity of 15.3 mPa by spin coating (acceleration rate of 415 RPM/s, final speed of 2000 RPM for 30 seconds), (ii) then heated on a hot plate at 100° C. for 10 minutes followed by (iii) exposure to UV (i.e., 254 nm germicidal lamp) in a nitrogen atmosphere for 15 minutes and then (iv) a post heating on a hotplate at 100° C. for 10 minutes. The ZrOAc solution comprised 8.5 wt % of SARTOMER™ SR-368, 40.0 wt % of zirconia nanoparticles surface treated with silane A-174 (as described in U.S. patent application Ser. Nos. 11/771,787 and 11/771,859), 1.5 wt % of IRGACURE™ 184 photoinitiator, and 50.0 wt % of isophorone.

Three samples were prepared on a substrate as described above using one of the following semiconductor ink formulations. For TIPS-pentacene, the ink formulation was a solution of 2.0 wt % TIPS-pentacene and 1 wt % polystyrene (PS) in n-butylbenzene. For allyl-DIPS, the ink formulation was a solution of 2.0 wt % allyl-DIPS and 1 wt % polystyrene (PS) in n-butylbenzene. For isopropenyl-DIPS (IP-DIPS), the ink formulation was a solution of 1.8 wt % isopropenyl-DIPS (IP-DIPS) and 1 wt % polystyrene (PS) in n-butylbenzene.

The ink solutions were filtered through a 0.2 micron filter and loaded into a print cartridge designed for a DIMATIX™ 2800 series ink jet printer (DMP, manufactured by Fujifilm Dimatix, Inc. (Santa Clara, Calif.)). A 30 mm×20 mm area was printed on each sample using the semiconductor ink with the following DMP parameters: a liquid crystalline polymer (LCP) cartridge having a drop volume of 10 picoliter (pL); a cartridge head temperature of 28° C.; a platen temperature of 30° C.; and a drop spacing of 20 micrometer (μm). An ink jet drop matrix of 1501×1001 drops was deposited onto the substrate, the drops wetted together such that the ink solution covered the area.

Figure 2:
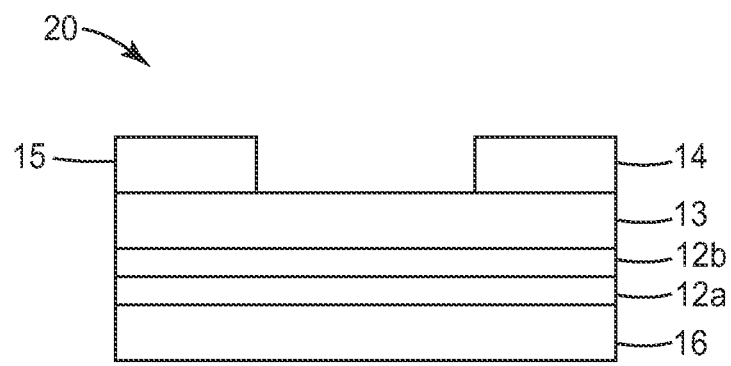
FIG. 2 is a cross-sectional view of another exemplary thin film transistor comprising a semiconductor layer formed via solution deposition of a composition containing at least one pentacene compound of the present invention.

The semiconductor layer was allowed to dry at room temperature and then approximately 1000 Angstroms of gold was vapor deposited through a shadow mask thereon to form an array of devices with individual constructions similar to exemplary device 20 shown in FIG. 2. (Although exemplary device 20 shown in FIG. 2 depicts gate electrode 16 as a single layer, in the present example, a three-layered structure, namely, a heavily doped n-type silicon wafer layer, an intermediate 100 Å TiN layer, and a lower 5000 Å aluminum layer represents the gate electrode of this exemplary device.)

The devices, made as described above with a channel length (L)=100 μm and a channel width (W)=1000 μm, gave the following charge carrier mobility values shown in Table 5 below as measured using Mobility Test Method I (i.e., using the TF&CCMV Test Method of the present invention).

TABLE 5

Comparison of Charge Carrier Mobility Value Measurements For Electronic Devices Comprising TIPS-pentacene, Allyl-DIPS and IP-DIPS

| | Charge Carrier Mobility Value ($cm^2$/V-s) | | |
|---|---|---|---|
| | TIPS-pentacene | Allyl-DIPS | IP-DIPS |
| minimum mobility value | 0.00498 | 0.00671 | 0.02159 |

TABLE 5-continued

Comparison of Charge Carrier Mobility Value Measurements
For Electronic Devices Comprising
TIPS-pentacene, Allyl-DIPS and IP-DIPS

| | Charge Carrier Mobility Value $(cm^2/V\text{-}s)$ | | |
|---|---|---|---|
| | TIPS-pentacene | Allyl-DIPS | IP-DIPS |
| maximum mobility value | 1.957 | 2.453 | 3.438 |
| average mobility value | 0.359 | 0.443 | 0.872 |

Example 5

Preparation of Electronic Device with Ag Top Contacts

An n-type silicon wafer with thermal oxide as in Example 4 was (i) washed with acetone and dried with $N_2$, (ii) washed with isopropyl alcohol (IPA) and dried with $N_2$, (iii) washed with deionized water (DI) water and dried with $N_2$, and (iv) then treated with UV generated ozone ($UV/O_3$) for 10 minutes. The sample was then spin coating with a solution of ZrOAc and cured as described in Example 4. A semiconductor ink was prepared consisting of a solution of 2.0 wt % TIPS-pentacene and 1 wt % polystyrene (PS) in n-butylbenzene. The ink solution was filtered through a 0.2 µm filter and loaded into a print cartridge designed for the DIMATIX dot matrix printer (DMP) used in Example 4.

A 30 mm×20 mm area was printed with semiconductor ink on this sample using the following DMP parameters: a LCP cartridge having a drop volume of 10 pL; a cartridge head temperature of 28° C.; a platen temperature of 30° C.; and a drop spacing of 20 um. An ink jet drop matrix of 1501×1001 drops was deposited onto the substrate; the drops wetted together such that the ink solution covered the area. The semiconductor layer was allowed to dry at room temperature followed by printing silver source and drain contacts at 304 dpi using a SPECTRA™ inkjet print head SM-128 having a 50 pL drop volume and Cabot silver ink. The sample was heated to 120° C. for 10 minutes. The sample gave a charge carrier mobility value of 0.08 to 0.122 $cm^2/V\text{-}s$ as measured by Mobility Test Method I.

Example 6

Preparation of Electronic Devices

Figure 5:
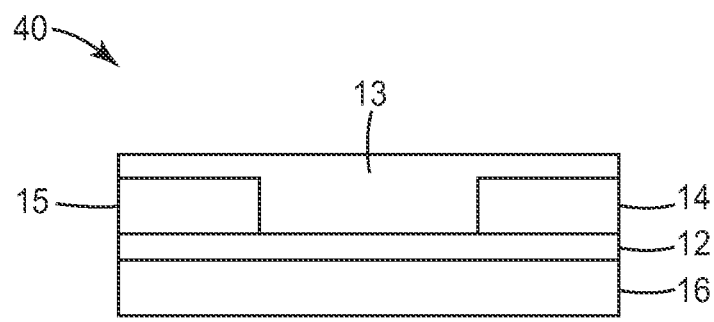
FIG. 5 is a cross-sectional view of yet another exemplary thin film transistor comprising a semiconductor layer formed via solution deposition of a composition containing at least one pentacene compound of the present invention.

Electronic devices having a construction as shown in FIG. 5 were prepared as follows. Heavily n-doped silicon wafers were used as gate electrode layer 16, while 250 nm of thermally-grown oxide served as dielectric layer 12. Source and drain electrodes 14 and 15 respectively were formed by evaporating gold or silver through a shadow mask under high vacuum conditions. The source and drain electrodes 14 and 15 respectively defined a channel with channel width, W, of 1,000 µm and channel length, L, of 100 µm. For the devices with gold electrodes, the substrates were cleaned by exposure to $UV/O_3$ for 15 min. at 85° C.

The electrode surfaces were treated with a number of thiol-based monolayers to improve crystallization of the semiconductor and shift metal work function to improve charge injection as disclosed in *IEEE Elect. Dev. Lett.* (2001), 22, 571 (Gundlach et al.), the subject matter of which is incorporated herein by reference in its entirety. Thiol-based monolayer treatments included, but were not limited to, octanethiol, dodecanethiol, decanedithiol, benzenethiol, 4-methoxybenzenethiol, pentachlorobenzenethiol, and pentafluorobenzenethiol. Typically, pentafluorobenzenethiol-treated electrodes yielded thin films with the best morphology.

The device substrate was then treated with hexamethyldisilazane (HMDS). Neat HMDS was deposited across the surface of the device, and was spun off under a blanket of nitrogen (1000 rpm for 30 s, then 4000 rpm for 120 s). The device substrate was then placed in a 120° C. oven for 2 minutes to anneal the monolayers.

A semiconductor layer 13 was deposited by drop-casting a 1 wt % solution of at least one pentacene compound of the present invention (dissolved in toluene, ethylbenzene, butylbenzene or chlorobenzene) over the source/drain electrodes. The solvent was allowed to evaporate slowly (by covering the substrate with a watch glass). Once the bulk of the solvent had evaporated and the semiconductor was clearly crystallized on the device surface, the substrate was placed in a 90° C. oven for 120 seconds to drive off the remaining solvent.

Each device was evaluated using Mobility Value Test Method II described above.
Typical device parameters for TIPS-pentacene were as follows:
charge carrier mobility values extracted from the linear regime varied from 0.001 to 0.45 $cm^2/Vs$;
threshold voltage varied from −2 to 11 V; and
on/off current ratio varied from $10^3$ to $10^6$.
Typical device parameters for DIIP-IPS pentacene on Au electrodes:
charge carrier mobility values extracted from the linear regime varied from 0.01 to 0.09 $cm^2/Vs$;
threshold voltage varied from 12 to −22 V; and
on/off current ratio varied from $10^2$ to $10^4$.
Typical device parameters for DIIP-IPS pentacene on Ag electrodes:
charge carrier mobility values extracted from the linear regime varied from 0.005 to 0.01 $cm^2/Vs$;
threshold voltage varied from 10 to −25 V; and on/off current ratio varied from $10^2$ to $10^5$.

Example 7

Synthesis of 6,13-Bis(cyclopropyldiisopropylsilyl-ethynyl)pentacene (Cyclopropyl DIP S-Pentacene)

Synthesis of Cyclopropyldiisopropylsilyl Acetylene

This material was synthesized using methods identical to those used to prepare allyldiisopropylsilyl acetylene in Example 1, simply substituting cyclopropyl magnesium bromide for allyl magnesium bromide. $^1$H-NMR (200 MHz, $CDCl_3$) δ=2.3 (s, 1H), 1.1 (br-m, 14H), 0.61 (m, 2H), 0.45 (m, 2H), −0.44 (m, 1H).

Synthesis of 6,13-Bis(cyclopropyldiisopropylsilyl-ethynyl)pentacene (Cyclopropyl DIPS-Pentacene)

This material was prepared using methods similar to those used to synthesize Allyl DIPS-pentacene in Example 1, simply substituting cyclopropyldiisopropylsilyl acetylene for allyldiisopropylsilyl acetylene. $^1$H-NMR (200 MHz, $CDCl_3$) δ=9.2 (s, 4H), 8.0 (dd, J=3.2, 5.6 Hz, 4H), 7.4 (dd, J=3.2, 5.6 Hz, 4H), 1.4 (br-m, 28H), 0.85 (m, 8H), −0.21 (m, 2H).

Example 8

Synthesis of 6,13-Bis((1-methylenepropyl)diisopropylsilylethynyl)pentacene (2-but-1-enyl DIPS acetylene)

Synthesis of (1-methylenepropyl)diisopropylsilyl Acetylene

This material was synthesized by methods identical to those used to prepare allyldiisopropylsilyl acetylene (Example 1), simply substituting 2-lithio-1-butene (generated in situ by treating 2-bromo-1-butene with n-BuLi in tetrahydrofuran at −78° C.) for allyl magnesium bromide. $^1$H-NMR (200 MHz, CDCl$_3$) δ=5.76 (q, J=1.2 Hz, 1H), 5.55 (quint, J=1.2 Hz, 1H), 2.41 (s, 1H), 1.06 (br. s, 14H), 2.19 (q, t, J=9.5, 1.2 Hz, 2H), 1.10 (t, J=9 Hz, 3H).

Synthesis of 6,13-Bis((1-methylenepropyl)diisopropylsilylethynyl)pentacene (2-but-1-enyl DIPS-Pentacene)

This material was prepared using methods similar to those used to synthesize Allyl DIPS-pentacene (Example 1), simply substituting (1-methylenepropyl)diisopropylsilyl acetylene for allyldiisopropylsilyl acetylene. $^1$H-NMR (200 MHz, CDCl$_3$) δ=9.33 (s, 4H), 7.98 (dd, J=3.4, 6.6 Hz, 4H), 7.41 (dd, J=3.4, 6.6 Hz, 4H), 5.9 (q, J=1 Hz, 2H), 5.83 (quint, J=1 Hz, 2H), 2.19 (q, t, J=8, 1.1 Hz, 4H), 1.39 (br. s, 28H), 1.24 (t, J=8 Hz, 6 H).

Example 9

Preparation of Electronic Device using Dip-Coating

A heavily doped n-type silicon wafer with 1000 Angstroms of thermal oxide as in Example 4 was used as a substrate. Substrates were treated for 3 minutes in a Plasma Cleaning System (Model YES-G1000 from Yield Engineering Systems, Inc. (Livermore, Calif.)) using a power setting of 500 W and oxygen flow of 1 standard cubic centimeter per minute (sccm). The sample was then (i) coated with a semiconductor solution using a dip-coating apparatus (NIMA D1L from Nima Technology LTD (Coventry, England)) using a draw speed of 3 mm/min., and (ii) then allowed to dry at room temperature. Approximately 800-1000 Angstroms of gold was vapor deposited thereon through a shadow mask. Transistors were then characterized according to Mobility Value Test Method I.

Each semiconductor solution was a 1.8-2.0 wt % solution in n-butylbenzene solvent, which had been filtered prior to use (Pall Life Sciences ACRODISC® CR 25 mm, 0.2 um PTFE syringe filter). The semiconductor solution was placed into a dip-coating tank approximately 50 mm wide, 5 mm deep, and 30 mm high. Approximately 5 mL of solution was used. After coating, long crystals were present on the SiO$_2$ surface of the substrate, and typically oriented parallel to the dip axis. Source and drain contacts were oriented relative to the semiconductor crystals such that the crystals bridged the contacts.

Semiconductors used in this example were: (i) TIPS-pentacene; (ii) 6,13-Bis-[(isopropenyldiisopropylsilyl)ethynyl]pentacene (IP-DIPS); (iii) 6,13-Bis[(allyl-diisopro-pylsilyl)ethynyl]pentacene (Allyl-DIPS); (iv) 6,13-Bis((1-methylenepropyl)diisopropyl-silylethynyl)pentacene (2-but-1-enyl DIPS); and (v) 6,13-Bis-[(cyclopropyldiisopropylsilyl)ethynyl]pentacene (Cyclopropyl DIPS).

Often dip-coating does not result in complete coverage of the substrate, so the effective channel width of the devices needed to be measured. The percentage of substrate surface covered by crystals was measured by (i) taking three digital photos of the substrate at high magnification (100×), then (ii) using a photo editing tool such as ADOBE® PHOTOSHOP® photo editing software to identify and render areas of exposed substrate as uniform black (0,0,0) coloration in L,a,b color space, then (iii) using the histogram feature of PHOTOSHOP® photo editing software to identify the percentage of photo with luminosity (L)<15, and then (iv) averaging the result of the three photos to give a value for surface coverage of the substrate. The value of surface coverage was then used to calculate the effective channel width of the TFTs, and this effective channel width was used to calculate charge carrier mobility values. The following formula was used to calculate effective channel width:

$$Weff = \left(\frac{Wdep}{100}\right) * Cov$$

where $W_{eff}$ is the effective channel width, $W_{dep}$ is the length of source and drain contacts (as-deposited), and $C_{ov}$ is the surface coverage (in percent). For example, if the source and drain electrodes were 1000 microns long and the surface coverage was 80 percent, then the effective channel width would be 800 microns.

Charge carrier mobility values for the semiconductors in this example are shown in Table 6 below and were measured using Mobility Value Test Method I described above.

TABLE 6

Comparison of Charge Carrier Mobility Value Measurements For Electronic Devices Comprising TIPS-pentacene, Allyl-DIPS, IP-DIPS, 2-but-1-enyl DIPS and Cyclopropyl DIPS

| | Charge Carrier Mobility Value (cm$^2$/V-s) | | | | |
|---|---|---|---|---|---|
| | TIPS-pentacene | Allyl-DIPS | IP-DIPS | 2-but-1-enyl DIPS | Cyclopropyl DIPS |
| minimum mobility value | 0.123 | 0.148 | 0.0991 | 0.127 | 0.104 |
| maximum mobility value | 0.176 | 0.417 | 0.201 | 0.387 | 1.46 |
| average mobility value | 0.155 | 0.265 | 0.147 | 0.286 | 0.559 |

Example 10

Synthesis of 6,13-Bis(cyclopropyldiisopropylsilylethynyl)-1-fluoro-pentacene

Synthesis of 1-fluoropentacenequinone

3-Fluoro-o-xylene (1.2 g, 9.7 mmol) was added to a round-bottom flask with a stir bar and dissolved in 30 mL dichloroethane. N-Bromosuccinimide (7.0 g, 39 mmol) and a small scoop of AIBN (2,2'-azobis(2-methylpropionitrile)) were added, a reflux condenser was attached, and the mixture was refluxed for 6 hr, at which point analysis by GC-MS showed the predominant component to be the tribrominated product. After cooling, water and dichloromethane were added, and the organic layer was separated, then washed with water and dilute hydrochloric acid, dried over magnesium sulfate, and rinsed through a thin pad of silica gel using dichloromethane as an eluent. Removal of solvent yielded 3.4 g of the product mixture. To a 100 mL round-bottom flask equipped with a condenser and stir bar, 12 mL dimethylformamide was added, followed by 0.54 g (2.07 mmol) of the tribrominated product from above and 0.43 g (2.1 mmol) 1,4-anthraquinone. Nitrogen was bubbled through the solution for 20 minutes, then 2.1 g (12 mmol) potassium iodide was added, and the reaction was heated at 110° C. for 3 days. The reaction was allowed to cool and the precipitate was collected by filtration, then rinsed sequentially with water, acetone and diethyl ether. The resulting solid was air-dried, yielding 0.29 g (0.88 mmol, 42%) of 1-fluoropentacenequinone as a light brown solid.

Synthesis of 6,13-Bis(cyclopropyldiisopropylsilyl-ethynyl)-1-fluoropentacene

A flame-dried 100 mL round-bottom flask (with stir bar) was cooled under nitrogen and placed in an ice bath. Into this flask was added 8 mL anhydrous THF and 1.5 g (8.3 mmol) (cyclopropyldiisopropylsilyl)acetylene from Example 7. n-Butyllithium (2.6 mL, 2.5 M in hexane) was added over 10 minutes. The reaction was allowed to stir 1 hour, then 0.98 g (3.0 mmol) 1-fluoropentacenequinone was added, and stirring continued overnight. Several drops of saturated ammonium chloride were added, followed by 5 mL methanol, and the solution was poured into a solution of 2.4 g (11 mmol) stannous chloride dihydrate and 2 mL 10% aqueous hydrochloric acid in 50 mL methanol and stirred for 10 minutes. Then, 30 mL methanol and 3 mL 10% aqueous hydrochloric acid were added, and stirring continued for 15 minutes, at which time 20 mL methanol was added and the solution was placed in the refrigerator for 3 hours. Filtration gave a blue solid, which was purified by chromatography on silica gel using hexane as an eluent. The resulting blue solid was then recrystallized from acetone, yielding 0.77 g (1.2 mmol, 39%) of product as blue needles. Analysis of the blue needles product provided the following data: 1H-NMR (400 MHz, CDCl3) δ=9.5 (s, 1H), 9.2 (s, 1H), 9.2 (s, 1H), 9.2 (s, 1H), 8.0 (dd, J=3.2 Hz, 6.8 Hz, 2H), 7.7 (d, J=8.8 Hz, 1H), 7.4 (dd, J=3.2 Hz, 6.4 Hz, 2H), 7.3 (m, 1H), 7.0 (m, 1H), 1.4 (m, 28H), 0.8 (m, 8H), −0.2 (m, 2H).

Example 11

Synthesis of 6,13-Bis(cyclopropyldiisopropylsilyl-ethynyl)-2.9(10)-difluoro-pentacene Synthesis of 2,9-Difluoropentacene-6,13-dione and 2,10-difluoropentacene-6,13-dione 4-Fluoro-o-xylene (5.7 g, 46 mmol) was added to a round-bottom flask with a stir bar and dissolved in 150 mL dichloroethane. N-Bromosuccinimide (33.1 g, 186 mmol) and a small scoop of AIBN (2,2'-azobis(2-methylpropionitrile)) were added, a reflux condenser was attached, and the mixture was refluxed for 6 hr. Analysis by GC-MS showed a 90:10 mixture of tribrominated to tetrabrominated product. After cooling, water and dichloromethane were added, and the organic layer was separated, then washed with water and dilute hydrochloric acid, dried over magnesium sulfate, and rinsed through a thin pad of silica gel using dichloromethane. Removal of solvent yielded 16.3 g of the product mixture, which was dissolved in 120 mL of dimethylformamide with benzoquinone (1.9 g, 18 mmol). This mixture was purged using nitrogen gas, then potassium iodide (40 g, 240 mmol) was added and the reaction mixture was heated to 110° C. for 4 days. The resulting precipitate was cooled, diluted with acetone, isolated by filtration, washed with additional acetone and water, then triturated from acetone to yield 1.3 g (3.7 mmol, 21%) product as a light brown solid.

Synthesis of 6,13-Bis(cyclopropyldiisopropylsilyl-ethynyl)-2.9(10)-difluoropenta-cene (Cyclopropyldiisopropylsilyl)acetylene (1.6 g, 8.8 mmol) and anhydrous THF (7 mL) were added to a dry 100-mL round bottom flask equipped with a stir bar and cooled in an ice bath. n-Butyllithium (3.0 mL, 2.5 M in hexane) was added dropwise, and the solution was stirred for 30 minutes. An isomeric mixture of the two quinones (2,9-difluoropenta-cene-6,13-dione and 2,10-difluoropentacene-6,13-dione) (1.1 g, 3.1 mmol) was added and stirring was continued for 12 hr. The reaction was quenched by the addition of 4 drops of saturated ammonium chloride, then diluted with methanol (20 mL). In a separate Erlenmeyer, stannous chloride dihydrate (2.1 g, 9.3 mmol) was dissolved in methanol (200 mL) and 10% aqueous hydrochloric acid (2 mL), then cooled in the refrigerator for 1 hr. With stirring, the quenched reaction mixture was poured in a slow stream into the cold methanol solution and stirred for 20 minutes, then placed back in the refrigerator for 1 hr. The solid was collected by filtration, air-dried, then taken up in 9:1 hexane:dichloromethane and rinsed through a thin pad of silica. Removal of solvent yielded a shiny blue powder, which recrystallized from acetone to yield blue needles (0.1 g, 5%). Analysis of the blue needles product provided the following data: 1H-NMR (200 MHz, CDCl3) δ=9.2 (s, 2H, isomer A, 2H, isomer B), 9.1 (s, 2H, isomer A, 2H isomer B), 8.0 (m, 2H, isomer A, 2H, isomer B), 7.5 (m, 2H, isomer A, 2H, isomer B), 7.2 (m, 2H, isomer A, 2H, isomer B, coincident with the chloroform signal), 1.4 (m, 28H), 0.8 (m, 8H), −0.2 (m, 2H).

Example 12

Synthesis of 6,13-Bis(cyclopropyldiisopropylsilyl-ethynyl)-1,8(11)-difluoro-pentacene Synthesis of 1,8-Difluoropentacene-6,13-dione and 1,11-difluoropentacene-6,13-dione 3-Fluoro-o-xylene (5.7 g, 46 mmol) was added to a round-bottom flask with a stir bar and dissolved in 150 mL dichloroethane. N-Bromosuccinimide (33.1 g, 186 mmol) and a small scoop of AIBN (2,2'-azobis(2-methylpropionitrile)) were added, a reflux condenser was attached, and the mixture was refluxed for 6 hr until analysis by GC-MS indicated that the primary product was the tribrominated adduct. After cooling, water and dichloromethane were added, and the organic layer was separated, then washed with water and dilute hydrochloric acid, dried over magnesium sulfate, and rinsed through a thin pad of silica gel using dichloromethane. Removal of solvent yielded 16.1 g of the product mixture. To a 100 mL round-bottom flask equipped with a condenser and stir bar, 12 mL dimethylformamide was added, followed by 1.1 g (~4.1 mmol) of the tribrominated product from above and 0.22 g (2.0 mmol) benzoquinone. Nitrogen was bubbled through the solution for 20 minutes, then 2.1 g (12 mmol) potassium iodide was added, and the reaction was heated at 110° C. for 3 days. The reaction was allowed to cool and the precipitate was collected by filtration, then rinsed sequentially with water, acetone and diethyl ether. The resulting solid was air-dried, yielding 0.15 g (0.42 mmol, 21%) of an isomer mixture of difluoropentacenequinone as a light brown solid.

Synthesis of 6,13-Bis(cyclopropyldiisopropylsilyl-ethynyl)-1,8(11)-difluoropenta-cene This material was prepared using methods similar to those used to synthesize 6,13-Bis(cyclopropyldiisopropylsilyl-ethynyl)-2.9(10)-difluoropentacene in Example 11 above, simply substituting the 1,8-Difluoropentacene-6,13-dione and 1,11-difluoropentacene-6,13-dione mixture for the 2,9-difluoropentacene-6,13-dione and 2,10-difluoropentacene-6,13-dione mixture. Analysis of the product provided the following data: 1H-NMR (200 MHz, CDCl3) δ=9.5 (s, 2H, isomer A), 9.2 (s, 2H, isomer B), 7.8 (s, 1H, isomer A), 7.7 (s, 1H, isomer B), 7.3 (m, 2H per isomer, isomer A and B), 7.0 (m, 2H per isomer, isomer A and B), 1.3 (m, 28H), 0.8 (m, 8H), −0.2 (m, 2H).

Example 13

Synthesis of 6,13-Bis(cyclopropyldiisopropylsilyl-ethynyl)-2,3,9,10-tetra-methylpentacene

Synthesis of 2,3,9,10-tetramethylpentacene-6,13-dione

To 1.6 grams (10 mmol) of 4,5-dimethyl phthalaldehyde in 20 mL ethanol was added 0.56 grams (5 mmol) of cyclohexane 1,4-dione. Upon complete dissolution of the starting materials, 2 drops of 15% aq. NaOH solution were added, and precipitation of the quinone began immediately. The suspension was stirred for a further 2 hours, then diluted with a 10-fold excess of methanol, and the solid collected by filtration. The solid quinone was washed with copious methanol, then ether, and was allowed to air-dry overnight. The quinone (1.5 g, 82%) was used without further purification.

Synthesis of 6,13-Bis(cyclopropyldlisopropylsilyl-ethynyl)-2,3,9,10-tetramethyl-pentacene A flame-dried 100-mL round-bottom flask (with stir bar) was cooled under nitrogen and placed in an ice bath. Via syringe, anhydrous THF (6 mL) was added, followed by 1.4 g (7.5 mmol) (cyclopropyldiisopropylsilyl)acetylene. n-Butyllithium(2,4 mL, 2.5 M in hexane) was added dropwise, and the reaction was allowed to stir for 1 hour, at which point 1.0 g (2.7 mmol) 2,3,9,10-tetramethylpentacene-6,13-dione was added. After stirring for 12 hr, 0.5 mL saturated ammonium chloride was added, followed by a cold solution of 1.9 g (8.5 mmol) stannous chloride dihydrate and 2 mL 10% aqueous hydrochloric acid in 6 mL MeOH. The resulting mixture was allowed to stir for 40 minutes. The mixture was then added to a solution of 3 mL 10% HCl in 100 mL MeOH, stirred for 10 more minutes, then placed in the refrigerator. After 2 hours, the green solution was removed, 0.5 g stannous chloride dihydrate and 1 mL 10% aqueous hydrochloric acid were added and stirred at room temperature for 15 minutes, then placed back in the refrigerator for 1.5 hours. The solution was then filtered, rinsed with MeOH, dissolved in DCM, and taken through a short plug of silica with DCM as an eluent. The resulting green solid was recrystallized from toluene, yielding 0.12 g (0.17 mmol, 6.5%) of the product as blue-green needles. Analysis of the blue-green needle product provided the following data: 1H-NMR (200 MHz, CDCl3) δ=9.0 (s, 4H), 7.7 (s, 4H), 2.5 (s, 12H), 1.3 (m, 28H), 0.8 (m, 8H), −0.2 (m, 2H).

Example 14

Synthesis of 6,13-Bis(cyclopropyldiisopropylsilyl-ethynyl)-2,3:9,10-bis(c-dihydrofurano)pentacene

Synthesis of 2,3:9,10-Bis(c-dihydrofurano)pentacene-6,13-dione 4,5-c-Dihydrofurano-1,2-dihydroxymethylbenzene was oxidized to the corresponding aldehyde using Swern conditions in 90% yield. The resulting 4,5-c-dihydrofurano-1,2-diformylbenzene was reacted with 0.5 equivalents of cyclohexane-1,4-dione in THF using 15% aqueous sodium hydroxide as catalyst for the quadruple aldol condensation to yield the desired quinone in 60-96%.

A flame-dried 100-mL round-bottom flask (with stir bar) was cooled under nitrogen and placed in an ice bath Into this flask was added 5 mL anhydrous THF and 0.90 g (5.0 mmol) (cyclopropyldiisopropylsilyl)acetylene. n-Butyllithium (2.0 mL, 2.2 M in cyclohexane) was added dropwise, and the solution was allowed to stir for 1 hr. 2, 3:9, 10-Bis(c-dihydrofurano)pentacene-6,13-dione (0.78 g, 2.0 mmol) was then added, and the reaction stirred for 12 hr. The reaction was quenched by the addition of 0.5 mL saturated ammonium chloride, followed by the addition of a cold solution of 1.6 g (7.0 mmol) stannous chloride dihydrate and 2 mL 10% aqueous hydrochloric acid in 5 mL methanol. The resulting mixture was stirred for 30 minutes in an ice bath. Subsequently, 1 mL 10% HCl in 150 mL MeOH was added. The solution was stirred for one hour and was placed in the refrigerator for 3 hours. Filtration gave the product as a blue-green solid, which was purified by chromatography using DCM as an eluent, then recrystallized twice from acetone, yielding blue needles (0.19 g, 0.26 mmol, 13%). Analysis of the blue needle product provided the following data: 1H-NMR (200 MHz, CDCl3) δ=9.1 (s, 4H), 7.8 (s, 4H), 5.2 (s, 8H), 1.4 (m, 28H), 0.8 (m, 8H), −0.2 (m, 2H).

Example 15

Synthesis of 6,13-Bis(allyl dicyclopropylsilylethynyl)-pentacene

Synthesis of (Allyldicyclopropylsilyl)Acetylene

To an oven-dried 250-mL round bottom flask was added (trimethylsilyl)acetylene (3.2 g, 33 mmol) and anhydrous THF (24 mL). The solution was cooled to 0° C., then n-butyllithium (11.6 mL, 29 mmol, 2.5 M in hexane) was added dropwise. The solution was stirred for 1 hr before the next step. In a separate oven-dried 250-mL round bottom flask, allyltrichlorosilane (5.13 g, 29.2 mmol) was dissolved in anhydrous THF (20 mL) and cooled in an ice bath. The second solution was equipped with an addition funnel, into which the first reaction mixture was added. The first reaction mixture was dripped into the second solution over a period of 30 minutes. The resulting solution was stirred overnight.

In a third oven-dried round bottom flask (500 mL) equipped with a condenser, 70 mmol cyclopropylmagnesium bromide was formed by the addition of an anhydrous diethyl ether solution of cyclopropyl bromide (9.1 g, 75 mmol, in 40 mL Et2O) to magnesium (1.7 g, 70 mmol) in anhydrous diethyl ether (7 mL), followed by refluxing for 4 hr. The newly formed Grignard reagent was then removed from the heat, and the crude allyldichloro(trimethylsilylethynyl)silane from the first step was added to this reagent, followed by refluxing overnight. The reaction was quenched by the addition of water, then dilute sulfuric acid to dissolve the salts, and extracted into hexane (2×50 mL). The organic layer was washed with water (5×20 m L) and brine, dried over magnesium sulfate, filtered, and concentrated under vacuum to yield a light brown liquid. Further purification by chromatography on silica gel with hexane as an eluent yielded the trimethylsilyl-capped product as a colorless liquid. The trimethylsilyl cap was removed by stirring in THF and MeOH with 3 drops of 15% sodium hydroxide solution for 30 minutes. After the addition of water, the product was extracted into hexane (2×50 mL), washed with water (3×20 mL), dried over magnesium sulfate, filtered, and concentrated under vacuum to yield 0.93 g (5.3 mmol, 18%) of a colorless liquid. Analysis of the colorless liquid product provided the following data: 1H-NMR (200 MHz, CDCl3) δ=5.9 (m, 1H), 4.9 (m, 2H), 2.3 (s, 1H), 1.7 (dt, J=8.2 Hz, 1.1 Hz, 2H), 0.6 (m, 4H), 0.4 (m, 4H), −0.4 (m, 2H).

Synthesis of 6,13-Bis(allyl dicyclopropylsilylethynyl)-pentacene

In an oven-dried 100-mL round bottom flask, (allyldicyclopropylsilyl)acetylene (1.5 g, 8.8 mmol) was dissolved in 9 mL of anhydrous THF, followed by the dropwise addition of ethylmagnesium chloride (3.5 mL, 7 mmol, 2 M in diethyl ether). The solution was heated to 60° C. for 1 hr, then removed from the heat. Pentacene quinone (0.94 g, 3.0 mmol) was added, then heating at 60° C. was resumed and continued for 12 hr. During that time, the reaction solidified. The reaction was quenched by the addition of 2 mL of a saturated ammonium chloride solution, which caused the solids to dissolve, then diluted with methanol (50 mL). In an Erlenmeyer flask, stannous chloride dihydrate (2.5 g, 12 mmol) was dissolved in methanol (200 mL), 10% hydrochloric acid solution (2 mL) was added, and the solution was chilled for 1 hr. Then, the quenched diol was added in a slow stream to the stannous chloride solution and stirred for 30 minutes, then chilled for 1 hr. The solid was filtered and rinsed with methanol, redissolved in minimal dichloromethane and diluted with hexane (about 9:1 hexane:dichloromethane), and rinsed through a pad of silica gel using 9:1 hexane:dichloromethane as an eluent. The solvent was removed to yield 750 mg of crude product as a blue solid, which was recrystallized from about 125 mL acetone to yield 0.58 g (0.92 mmol, 30% from quinone) blue needles. Analysis of the blue needle product provided the following data: 1H-NMR (200 MHz, CDCl3) δ=9.2 (s, 4H), 8.0 (dd, J=3.3 Hz, 4H), 7.4 (dd, J=3.3 Hz, 6.6 Hz, 4H), 6.2 (m, 2H), 5.2 (m, 4H), 2.0 (dt, J=8.2 Hz, 1.1 Hz, 4H), 0.83 (m, 16H), −0.025 (m, 2H).

Example 16

Synthesis of 6,13-Bis((2-methyl-1,3-dithiane)diisopropylsilylethynyl)-pentacene

Synthesis of Diisopropyl(trimethylsilylethynyl)silane

A flame-dried 250-mL round-bottom flask was cooled under nitrogen and placed in an ice bath. Into this flask was added 30 mL pentane and 3.6 g (36 mmol) trimethylsilylacetylene. n-Butyllithium (13.2, 2.5 M in hexane) was added over 12 minutes, and the reaction was allowed to stir for one hour at 0° C. Diisopropylchlorosilane (5.1 g, 34 mmol) was then added, and the reaction stirred overnight. The solution was extracted with pentane (2×40 mL) and the organic layers were washed with water, dried over magnesium sulfate, filtered, then carefully concentrated using rotary evaporation (product was volatile). Chromatography on silica with pentane as an eluent yielded 6.9 g (33 mmol, 99%) the desired product as a clear oil.

Synthesis of Diisopropyl(trimethylsilylethynyl)silyl Bromide

Diisopropyl(trimethylsilylethynyl)silane (6.9 g, 33 mmol) was dissolved in dichloroethane (20 mL) in a round-bottom flask equipped with a stir bar and placed in an ice bath. N-Bromosuccinimide (36 mmol, 6.5 g) was added scoopwise over 30 minutes, and stirring was continued for 15 more minutes or until the solution began to turn bright orange. Solvent was removed using rotary evaporation, pentane was added to the resulting solid, and the remaining solid succinimide residues were removed by filtration. The pentane solution was again evaporated, the process repeated, and the pentane was removed to yield 8.6 g (29 mmol, 89%) of a product as a pale brown oil.

Synthesis of ((2-Methyl-1,3-dithiane)diisopropylsilyl)acetylene

A 250 mL round-bottom flask with stir bar was flame-dried, cooled under nitrogen, and placed in an ice bath. To this flask was added 20 mL heptane, 10 mL anhydrous diethyl ether, and 5.0 g (37 mmol) 2-methyl-1,3-dithiane via syringe. n-Butyllithium (14.9 mL, 2.5 M in hexane) was added via syringe over 30 minutes. The solution was allowed to stir for 1.5 hr at 0° C., and was then placed in a water bath at room temperature and allowed to stir for another 1.5 hr, then placed back in the ice bath. Diisopropyl (trimethylsilylethynyl)silyl bromide (15.1 g, 51.0 mmol) dissolved in 10 mL heptane was then added over 6 minutes via syringe, and the reaction was allowed to stir overnight. The reaction mixture was poured into a saturated ammonium chloride solution, then extracted into hexane (2×50 mL) and washed with water and brine. The organic layer was dried with magnesium sulfate, filtered, and concentrated under rotary evaporation. The crude product was purified by chromatography using a 2:1 hexane:dichloromethane solution as an eluent, yielding 3.6 g (11 mmol, 29%) of the trimethylsilyl-capped acetylene as a clear oil. This acetylene was taken up in 24 mL of a 1:1 solution of methanol and THF, then 3 drops of 15% aqueous sodium hydroxide solution were added and the reaction was allowed to stir at room temperature for 30 minutes. Hexane and water were added, and allowed to stir for another 30 minutes. The resulting solution was extracted into hexane (2×30 mL), and the organic layers were combined, washed with water and dried over magnesium sulfate. After evaporating solvent, the crude product was purified by chromatography using 2:1 hexane:dichloromethane as an eluent, yielding 2.2 g (8.0 mmol, 22% overall from beginning 2-methyl-1,3-dithiane) of the product as a clear oil. Analysis of the clear oil product provided the following data: 1H-NMR (200 MHz, CDCl3) δ=3.3 (m, 2H), 2.5 (m, 2H), 2.5 (s, 1H), 2.0 (m, 3H), 1.6 (m, 2H), 1.4 (m, 14H).

Synthesis of 6,13-Bis((2-methyl-1,3-dithiane)diisopropylsilylethynyl)pentacene

In an oven-dried 100-mL round bottom flask, ((2-methyl-1,3-dithiane)diisopropyl-silyl)acetylene (1.5 g, 5.6 mmol)

was dissolved in anhydrous THF (8 mL) and cooled in an ice bath. n-Butyllithium (1.34 mL, 2.5 M in hexane) was added dropwise and the solution was stirred for 30 minutes, then pentacene quinone (0.44 g, 1.4 mmol) was added and stirring was continued for 12 hr. The reaction was quenched by the addition of 3 drops of a saturated ammonium chloride solution, then a solution of stannous chloride dihydrate (1.3 g, 6.2 mmol) in 2 mL aqueous hydrochloric acid was added and the reaction was stirred for 10 minutes. Dichloromethane (20 mL) and water (25 mL) were added and the entire solution was flushed through CELITE™ filter material using additional dichloromethane. The organic layer was separated, then dried over magnesium sulfate, filtered, and concentrated under rotary evaporation. The resulting oil was taken up in 1:1 dichloromethane:hexane, rinsed onto a medium pad of silica gel, and the blue product was eluted using the same solvent mixture. Removal of solvent yielded a thick blue oil, that yielded a blue solid, upon the addition of pentane. This solid was collected from the light blue solution, then recrystallized from toluene to yield 0.11 g (0.13 mmol, 9%) of product as blue plates. Analysis of the blue product provided the following data: 1H-NMR (200 MHz, CDCl3) δ=9.4 (s, 4H), 7.9 (dd, J=3.2 Hz, 6.6 Hz, 4H), 7.4 (dd, J=3.2 Hz, 6.6 Hz, 4H), 3.2 (m, 4H), 2.7 (m, 4H), 2.3 (s, 6H), 2.1 (unidentifiable multiplet), 1.7 (m, 2H), 1.5 (m, 28H).

Example 17

Synthesis of 6,13-Bis-((3-heptafluoroisopropoxy)propyldiisopropylsilyl-ethynyl)pentacene Synthesis of ((3-heptafluoroisopropoxy)propyldiisopropylsilyl)acetylene In a dried 250-mL round bottom flask, (3-heptafluoroisopropoxy)propyl-trichlorosilane (4.87 g, 13.5 mmol) was dissolved in anhydrous THF (15 mL). The solution was cooled in an ice bath, and isopropyllithium (41 mL, 28 mmol, 0.7 M in pentane) was added dropwise over 1 hr, followed by warming to room temperature over 12 hr. Ethynylmagnesium bromide (35 mL, 17 mmol, 0.5 M in THF) was added and the solution was heated to 60° C. for 12 hr. The reaction was quenched by the slow addition of water, then dilute sulfuric acid was added to dissolve the magnesium salts. The mixture was extracted into hexane (2×50 mL), washed with water (5×10 mL), dried over magnesium sulfate, filtered, and concentrated. The product was purified using chromatography on silica gel with hexane as an eluent (Rf~0.6 in hexane), resulting in 2.4 g (6.5 mmol, 48%) of a colorless liquid. Analysis of the colorless liquid product provided the following data: 1H-NMR (200 MHz, CDCl3) δ=4.0(t, J=6.2 Hz, 2H), 2.4 (s, 1H), 1.8 (m, 2H), 1.0 (m, 14H), 0.6 (m, 2H).

Synthesis of 6,13-Bis-((3-heptafluoroisopropoxy)propyldiisopropylsilylethynyl)-pentacene In an oven-dried 100-mL round bottom flask, ((3-heptafluoroisopropoxy)-propyldiisopropylsilyl)acetylene (2.0 g, 5.4 mmol) was dissolved in anhydrous THF (5 mL), then cooled in an ice bath. n-Butyllithium (1.8 mL, 4.5 mmol, 2.5 M in hexane) was added dropwise, and the solution was stirred in the bath for 30 minutes. Pentacene quinone (0.57 g, 1.8 mmol) was added, and the reaction was stirred for 12 hr. In a separate Erlenmeyer flask, stannous chloride dihydrate (1.4 g, 6.4 mmol) was dissolved in methanol (100 mL), and 1 mL of a 10% hydrochloric acid solution was added, then this solution was refrigerated for 1 hr. The reaction mixture was quenched by the addition of 0.5 mL of a saturated ammonium chloride solution, then diluted with methanol (20 mL). The quenched reaction mixture was poured in a slow stream into the stannous chloride mixture with stirring, and rinsed in with additional methanol. Stirring was continued for 30 minutes, then the entire mixture was refrigerated for 3 hr. The solid was removed by filtration, dried in ambient atmosphere, then purified using chromatography on silica gel with 9:1 hexane:dichloromethane as an eluent to yield 0.68 g of a blue solid. Recrystallization from acetone (~30 mL) yielded 0.6 g (0.6 mmol, 34%) product as burgundy plates. Analysis of the burgundy product provided the following data: 1H-NMR (200 MHz, CDCl$_3$) δ=9.2 (s, 4H), 7.9 (dd, J=3.4 Hz, 7.0 Hz, 4H), 7.4 (dd, J=3.4 Hz, 7.0 Hz, 4H), 4.1 (t, J=6.0 Hz, 4H), 2.1 (m, 4H), 1.3 (m, 28H), 1.0 (m, 4H).

Example 18

Preparation of Electronic Device using Dip-Coating

A heavily doped n-type silicon wafer with 1000 Angstroms of thermal oxide as in Example 4 was used as a substrate. Substrates were treated for 3 minutes in a Plasma Cleaning System (Model YES-G1000 from Yield Engineering Systems, Inc. (Livermore, Calif.)) using a power setting of 500 W and oxygen flow of 1 standard cubic centimeter per minute (sccm). The sample was then (i) coated with a semiconductor solution using a dip-coating apparatus (NIMA D1L from Nima Technology LTD (Coventry, England)) using a draw speed of 3 mm/min., and (ii) then allowed to dry at room temperature. Approximately 800-1000 Angstroms of gold was vapor deposited thereon through a shadow mask. Transistors were then characterized according to Mobility Value Test Method I.

Each semiconductor coating solution was a 2.0 wt % semiconductor and 1 wt % polystyrene (PS) in a solvent blend comprising 91 wt % n-butylbenzene and 9 wt % decane. The semiconductor solution had been filtered prior to use (Pall Life Sciences ACRODISC® CR 25 mm, 0.2 um PTFE syringe filter). The semiconductor solution was placed into a dip-coating tank approximately 50 mm wide, 5 mm deep, and 30 mm high. Approximately 5 mL of solution was used. After coating, long crystals were present on the SiO$_2$ surface of the substrate, and typically oriented parallel to the dip axis. Source and drain contacts were oriented relative to the semiconductor crystals such that the crystals bridged the contacts.

Semiconductors used in this example were: (i) 6,13-Bis[(allyl dicyclopropylsilyl)-ethynyl]pentacene (A-DCPS) and (ii) 6,13-Bis-[(cyclopropyldiisopropylsilyl)ethynyl]-pentacene (Cyclopropyl DIPS).

Effective channel width was measured as in Example 9 for the purposes of mobility calculation. Charge carrier mobility values for the semiconductors in this example are shown in Table 7 below and were measured using Mobility Value Test Method I described above.

TABLE 7

Comparison of Charge Carrier Mobility Value Measurements For Electronic Devices Comprising A-DCPS and Cyclopropyl DIPS

| | Charge Carrier Mobility Value (cm$^2$/V-s) | |
| --- | --- | --- |
| | A-DCPS | Cyclopropyl DIPS |
| minimum mobility value | 0.78 | 0.192 |

TABLE 7-continued

Comparison of Charge Carrier Mobility Value Measurements
For Electronic Devices Comprising A-DCPS and Cyclopropyl DIPS

| | Charge Carrier Mobility Value (cm$^2$/V-s) | |
|---|---|---|
| | A-DCPS | Cyclopropyl DIPS |
| maximum mobility value | 1.05 | 4.47 |
| average mobility value | 0.92 | 1.54 |

Example 19

Thermal Analysis of Materials

TIPS Pentacene is known to exhibit a crystal transformation at about 124° C. and, upon melting at about 266° C., exhibit an irreversible reaction, which is suspected to be a Diels-Alder reaction between an acetylene in the side group of one molecule and the aromatic structure of another molecule forming, at a minimum, a dimer. These transitions and reactions are readily observed using differential scanning calorimetry (DSC). For TIPS Pentacene in an upward temperature ramp, evident are an endotherm at ~124° C. (a solid-solid crystal transition) and the onset of an endotherm at ~266° C. (solid-liquid transition) which is overcome by the exotherm (Diels-Alder reaction). If the temperature ramp is terminated after the evolution of the endotherm at 124° C. and a downward temperature ramp is executed, the solid-solid transformation is shown to be reversible by the exotherm that occurs. If the dimer is formed by heating in excess of 266° C., the downward temperature ramp no longer shows evidence of this transition.

In some applications it may be advantageous to use materials for which these transitions are either not present or of a temperature well above the expected operational temperature range of devices fabricated using these semiconductor materials.

DSC characterization of 6,13-Bis(isopropenyldiisopropylsilylethynyl)pentacene, 6,13-Bis(allyl dicyclopropylsilylethynyl)-pentacene and 6,13-Bis(cyclopropyl-diisopropylsilylethynyl)-2,3,9,10-tetramethyl-pentacene indicated that these compounds do not have a low temperature solid-solid transition. The thermal transitions of these compounds as determined by DSC are given in Table 8 below.

TABLE 8

Comparison of Thermal Transitions for Some Organic Semiconductors.

| Compound | Example number | Compound Name | Solid-Solid (° C.) | Solid-Liquid (° C.) | Irreversible Exotherm (° C.) |
|---|---|---|---|---|---|
| II | | 6,13-Bis(triisopropylsilylethynyl)pentacene | 124.0 | 266.0 | upon melt |
| II | 2 | 6,13-Bis(isopropenyldiisopropylsilylethynyl)pentacene | | 237.0 | upon melt |
| LV | 15 | 6,13-Bis(allyl dicyclopropylsilylethynyl)-pentacene | | 199.1 | upon melt |
| LXIII | 13 | 6,13-Bis(cyclopropyldiisopropylsilylethynyl)-2,3,9,10-tetramethyl-pentacene | | 373.0 | upon melt |

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A pentacene compound having a chemical structure:

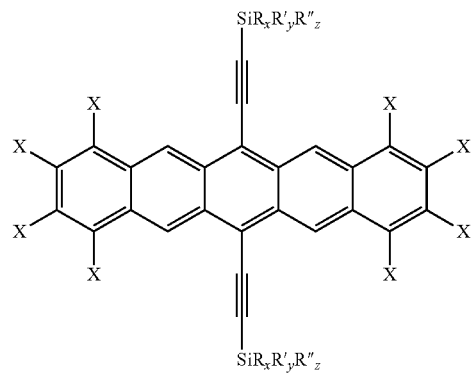

wherein:
each R independently comprises (i) a branched or unbranched, substituted or unsubstituted C3-C4 alkyl group, or (ii) a substituted or unsubstituted cyclopropyl group;
each R' independently comprises (i) a branched or unbranched, substituted or unsubstituted C3-C4 alkenyl group, or (ii) a substituted or unsubstituted cyclopropyl group;
R" comprises (i) hydrogen, (ii) a branched or unbranched, substituted or unsubstituted alkynyl group, (iii) a substituted or unsubstituted cyclopropyl, cyclobutyl or cyclopentyl group, (iv) a substituted or unsubstituted cyclopropylalkylene, cyclobutylalkylene or cyclopentylalkylene group, (v) a substituted or unsubstituted arylalkylene group, (vi) an acetyl group, or (vii) a substituted or unsubstituted heterocyclic ring comprising at least one of O, N, S and Se in the ring;
x=1 or 2;
y=1 or 2;
z=0;
(x+y+z)=3;
R and R' together comprise two identical groups and one dissimilar group; and
each X independently comprises hydrogen, wherein said pentacene compound enables formation of a semiconductor layer having a maximum charge carrier mobility value greater than or equal to 2.0 cm$^2$/V-s as measured by the Transistor Fabrication & Charge Carrier Mobility Value Test Method.

2. The pentacene compound of claim 1, wherein said pentacene compound comprises one of:

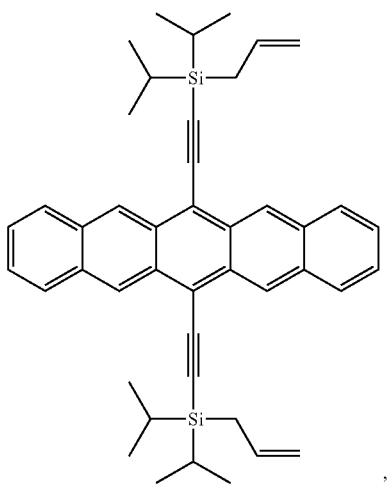 [SMILES: C=CC[Si](C#Cc1c2cc3ccccc3cc2c(C#C[Si](CC=C)(C(C)C)C(C)C)c2cc3ccccc3cc12)(C(C)C)C(C)C]
,

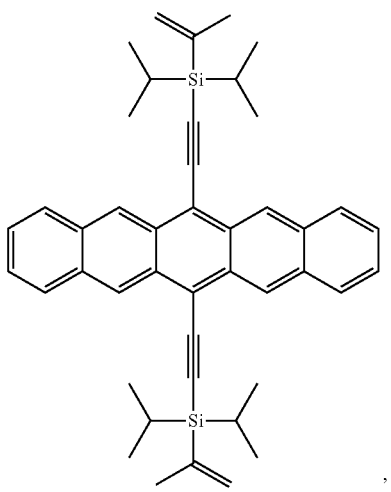
,

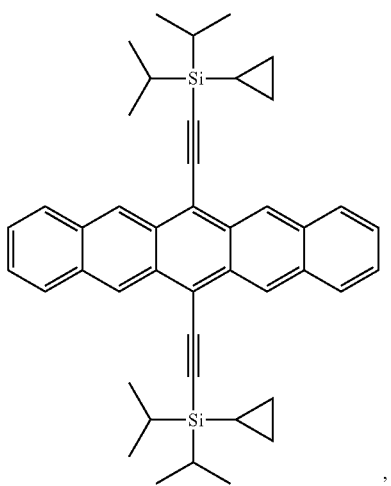
,

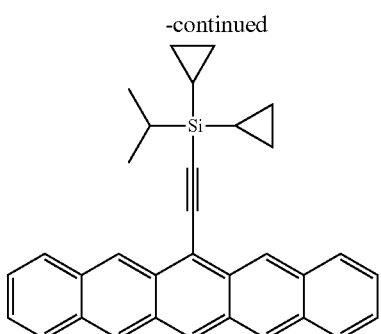

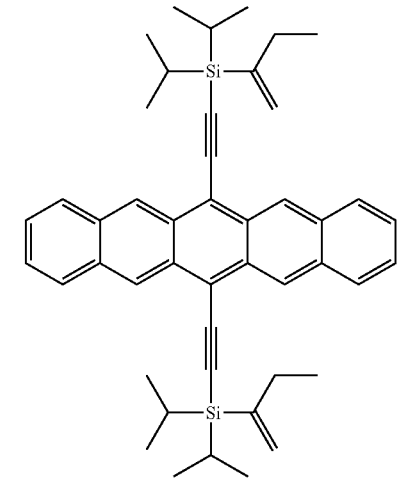
or

3. An electronic device comprising a coated layer, said coated layer comprising:

a pentacene compound having a chemical structure:

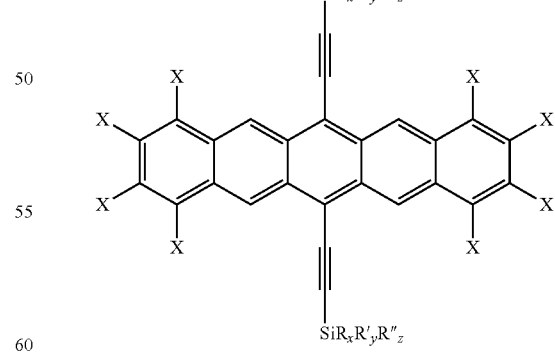

wherein:
  each R independently comprises (i) a branched or unbranched, substituted or unsubstituted C3-C4 alkyl group, or (ii) a substituted or unsubstituted cyclopropyl group;

each R' independently comprises (i) a branched or unbranched, substituted or unsubstituted C3-C4 alkenyl group, or (ii) a substituted or unsubstituted cyclopropyl group;

R" comprises (i) hydrogen, (ii) a branched or unbranched, substituted or unsubstituted alkynyl group, (iii) a substituted or unsubstituted cyclopropyl, cyclobutyl or cyclopentyl group, (iv) a substituted or unsubstituted cyclopropylalkylene, cyclobutylalkylene or cyclopentylalkylene group, (v) a substituted or unsubstituted arylalkylene group, (vi) an acetyl group, or (vii) a substituted or unsubstituted heterocyclic ring comprising at least one of O, N, S and Se in the ring;

x=1 or 2;
y=1 or 2;
z=0;
(x+y+z)=3;
R and R' together comprise two identical groups and one dissimilar group; and
each X independently comprises hydrogen;
said electronic device having a charge carrier mobility value greater than or equal to 2.0 cm²/V-s.

4. The electronic device of claim 3, wherein said coated layer further comprises a polymer.

5. The electronic device of claim 4, wherein the polymer is selected from the group consisting of polystyrene, poly(alpha-methylstyrene), poly(methyl methacrylate), poly(4-cyanomethyl styrene), poly(4-vinylphenol), and combinations thereof.

6. The electronic device of claim 3, wherein the charge carrier mobility value is measured using the Transistor Fabrication & Charge Carrier Mobility Value Test Method.

7. The electronic device of claim 6, wherein said electronic device has a charge carrier mobility value greater than or equal to 2.4 cm²/V-s as measured using the Transistor Fabrication & Charge Carrier Mobility Value Test Method.

8. The electronic device of claim 7, wherein said electronic device has a charge carrier mobility value greater than or equal to 3.4 cm²/V-s as measured using the Transistor Fabrication & Charge Carrier Mobility Value Test Method.

9. The electronic device of claim 3, wherein said pentacene compound comprises:

10. The electronic device of claim 3, wherein said pentacene compound comprises:

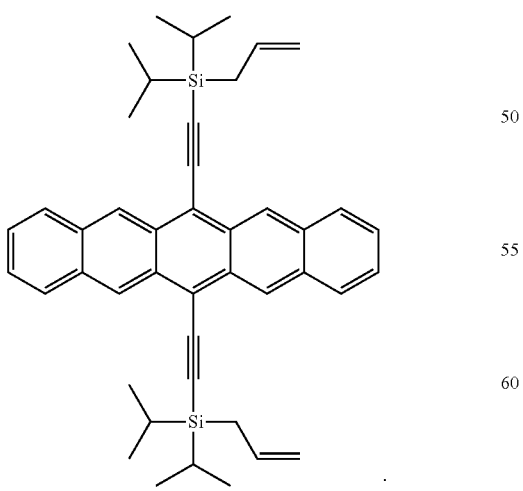

11. The electronic device of claim 3, wherein said pentacene compound comprises:

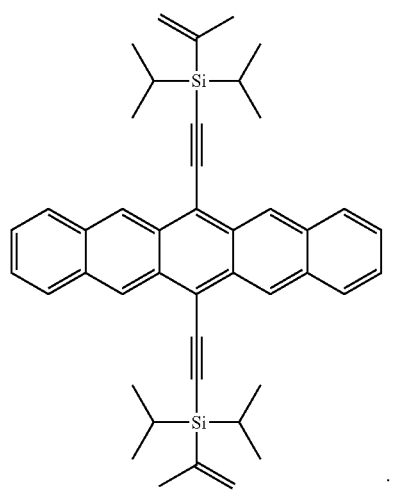 [SMILES: C=C(C)[Si](C#Cc1c2cc3ccccc3cc2c(C#C[Si](C(=C)C)(C(C)C)C(C)C)c2cc3ccccc3cc12)(C(C)C)C(C)C]

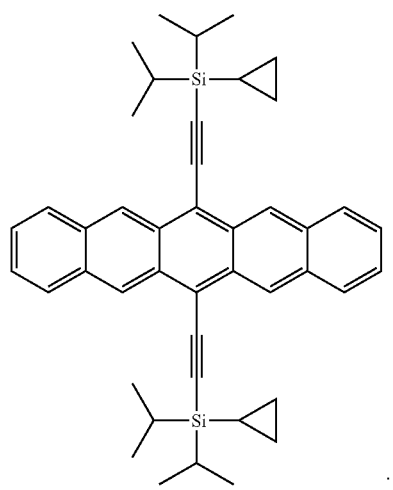 [SMILES: CC(C)[Si](C#Cc1c2cc3ccccc3cc2c(C#C[Si](C(C)C)(C(C)C)C2CC2)c2cc3ccccc3cc12)(C(C)C)C1CC1]

12. The electronic device of claim 3, wherein said pentacene compound comprises:

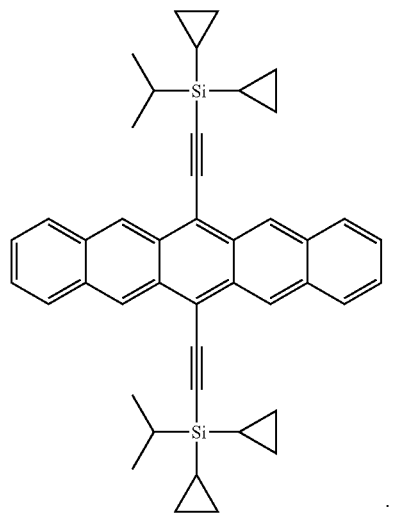 [SMILES: CC(C)[Si](C#Cc1c2cc3ccccc3cc2c(C#C[Si](C(C)C)(C2CC2)C2CC2)c2cc3ccccc3cc12)(C1CC1)C1CC1]

13. The electronic device of claim 3, wherein said pentacene compound comprises:

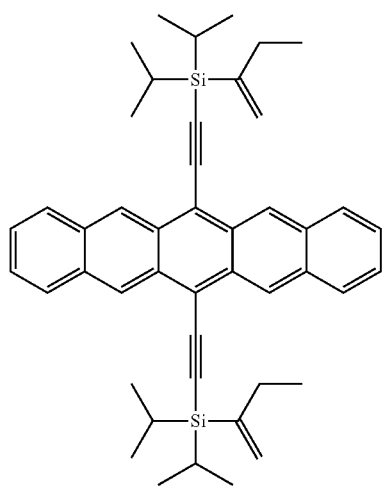

14. A pentacene compound having a chemical structure:

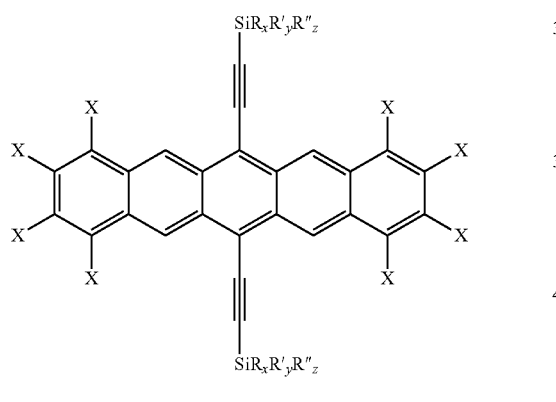

wherein:
each R independently comprises (i) a branched or unbranched, substituted or unsubstituted C3-C4 alkyl group, or (ii) a substituted or unsubstituted cyclopropyl group;
each R' independently comprises (i) a branched or unbranched, substituted or unsubstituted C3-C4 alkenyl group, or (ii) a substituted or unsubstituted cyclopropyl group;
R" comprises (i) hydrogen, (ii) a branched or unbranched, substituted or unsubstituted alkynyl group, (iii) a substituted or unsubstituted cyclopropyl, cyclobutyl or cyclopentyl group, (iv) a substituted or unsubstituted cyclopropylalkylene, cyclobutylalkylene or cyclopentylalkylene group, (v) a substituted or unsubstituted arylalkylene group, (vi) an acetyl group, or (vii) a substituted or unsubstituted heterocyclic ring comprising at least one of O, N, S and Se in the ring;
x=1 or 2;
y=1 or 2;
z=0;
(x+y+z)=3;
R and R' together comprise two identical groups and one dissimilar group; and
each X independently comprises hydrogen.

15. The pentacene compound of claim 14, wherein said pentacene compound comprises one of:

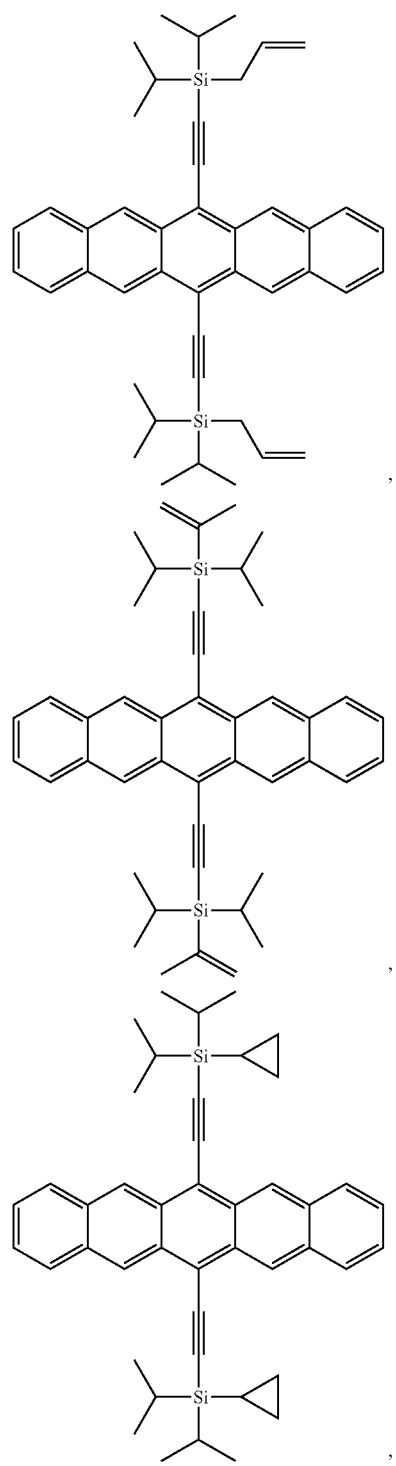

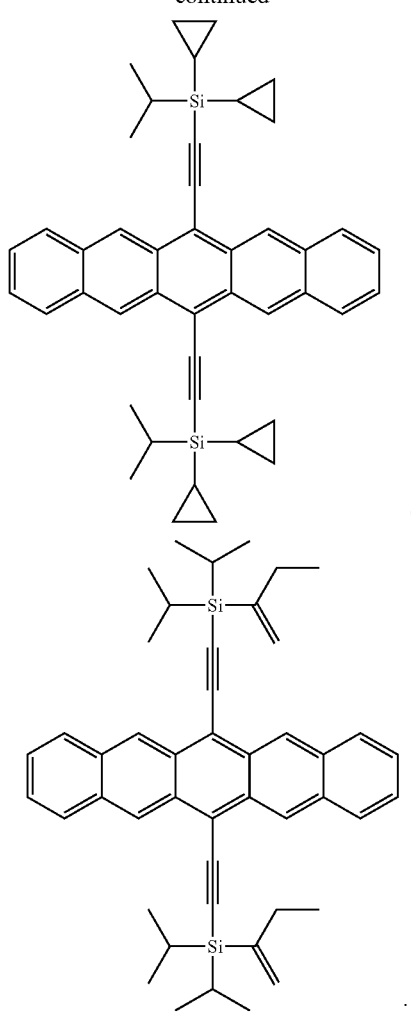
16. The pentacene compound of claim 15, wherein said pentacene compound comprises:
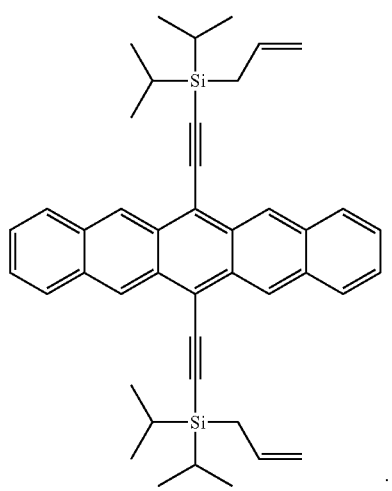 [SMILES: C=CC[Si](C#Cc1c2cc3ccccc3cc2c(C#C[Si](CC=C)(C(C)C)C(C)C)c2cc3ccccc3cc12)(C(C)C)C(C)C]
17. The pentacene compound of claim 15, wherein said pentacene compound comprises:
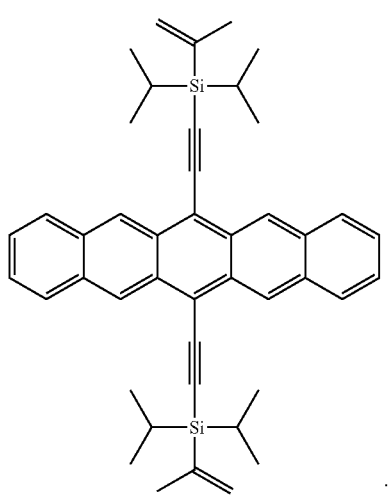 [SMILES: C=C(C)[Si](C#Cc1c2cc3ccccc3cc2c(C#C[Si](C(=C)C)(C(C)C)C(C)C)c2cc3ccccc3cc12)(C(C)C)C(C)C]
18. The pentacene compound of claim 15, wherein said pentacene compound comprises:
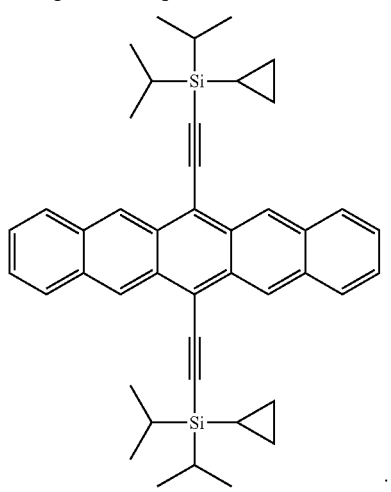
19. The pentacene compound of claim 15, wherein said pentacene compound comprises:
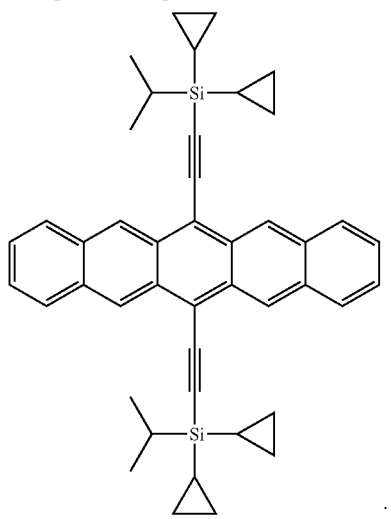 [SMILES: CC(C)[Si](C#Cc1c2cc3ccccc3cc2c(C#C[Si](C(C)C)(C2CC2)C2CC2)c2cc3ccccc3cc12)(C1CC1)C1CC1]

20. The pentacene compound of claim 15, wherein said pentacene compound comprises:
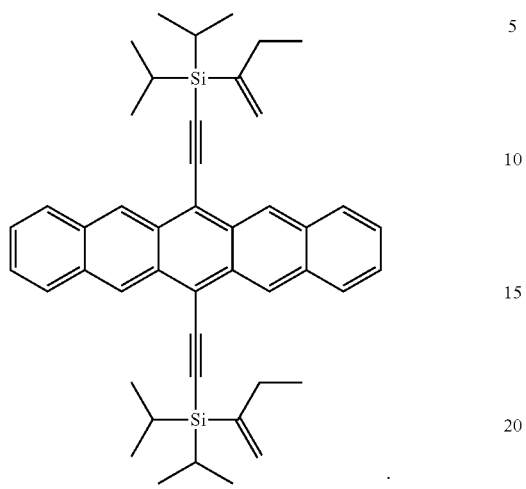

UNITED STATES PATENT AND TRADEMARK OFFICE
CERTIFICATE OF CORRECTION

PATENT NO. : 8,956,555 B2
APPLICATION NO. : 12/995145
DATED : February 17, 2015
INVENTOR(S) : Caldwell et al.

Page 1 of 1

It is certified that error appears in the above-identified patent and that said Letters Patent is hereby corrected as shown below:

Title Page

Page 2, column 1, under OTHER PUBLICATIONS, line 2, delete "Funtionalized" and insert therefor --Functionalized--, Page 2, column 1, under OTHER PUBLICATIONS, line 2, delete "Hexancene" and insert therefor --Hexacene--, Page 2, column 2, line 30, delete "Funtionalized" and insert therefor --Functionalized--, Page 2, column 2, line 30, delete "Hexancene" and insert therefor --Hexacene--, Page 2, column 2, line 42, delete "Copolymers" and insert therefor --Copolymers--, Page 2, column 2, line 51, delete "thiopheses" and insert therefor --thiophenes--, Page 2, column 2, line 53, delete "Funtionalized" and insert therefor --Functionalized--, Specification Column 23, line 56, delete "dihydrofur-ano" and insert therefor --dihydrofurano--, Column 28, line 64, delete "Alburquerque" and insert therefor --Albuquerque--, Column 36, line 48, delete "DIP S" and insert therefor --DIPS--, Column 40, line 8, delete "difluoropenta-cene" and insert therefor --difluoropentacene--, and Column 41, line 6, delete "difluoropenta-cene" and insert therefor --difluoropentacene--.

Signed and Sealed this
Twenty-fourth Day of November, 2015

Michelle K. Lee
*Director of the United States Patent and Trademark Office*